US011162127B2

(12) United States Patent
Heindl et al.

(10) Patent No.: US 11,162,127 B2
(45) Date of Patent: Nov. 2, 2021

(54) ENZYMATIC ONE-POT REACTION FOR DOUBLE POLYPEPTIDE CONJUGATION IN A SINGLE STEP

(71) Applicant: Hoffmann-La Roche Inc., Little Falls, NJ (US)

(72) Inventors: Dieter Heindl, Munich (DE); Erhard Kopetzki, Penzberg (DE); Georg Tiefenthaler, Sindelsdorf (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 153 days.

(21) Appl. No.: 15/625,918

(22) Filed: Jun. 16, 2017

(65) Prior Publication Data

US 2017/0314055 A1 Nov. 2, 2017

Related U.S. Application Data

(63) Continuation of application No. PCT/EP2015/079692, filed on Dec. 15, 2015.

(30) Foreign Application Priority Data

Dec. 17, 2014 (EP) ..................... 14198534

(51) Int. Cl.
| | |
|---|---|
| *C12P 21/02* | (2006.01) |
| *C07K 16/00* | (2006.01) |
| *C07K 16/32* | (2006.01) |
| *C07K 16/46* | (2006.01) |

(52) U.S. Cl.
CPC ............. *C12P 21/02* (2013.01); *C07K 16/00* (2013.01); *C07K 16/32* (2013.01); *C07K 16/468* (2013.01); *C12Y 304/2207* (2013.01); *C07K 2317/24* (2013.01); *C07K 2317/40* (2013.01); *C07K 2317/52* (2013.01); *C07K 2317/55* (2013.01); *C07K 2317/64* (2013.01)

(58) Field of Classification Search
CPC . C12P 21/02; C12Y 304/2207; C07K 16/468; C07K 16/32; C07K 16/00; C07K 2317/40; C07K 2317/64; C07K 2317/52; C07K 2317/24; C07K 2317/55
See application file for complete search history.

(56) References Cited

U.S. PATENT DOCUMENTS

| 8,247,198 B2 | 8/2012 | Gorke et al. |
|---|---|---|
| 10,864,277 B2 | 12/2020 | Grawunder et al. |
| 2009/0117628 A1 | 5/2009 | Gorke et al. |
| 2014/0030697 A1 | 1/2014 | Ploegh et al. |
| 2014/0057317 A1 | 2/2014 | Liu et al. |
| 2015/0152134 A1 | 6/2015 | Pentelute et al. |
| 2016/0082046 A1 | 3/2016 | Lodish et al. |
| 2016/0193355 A1 | 7/2016 | Qin et al. |

FOREIGN PATENT DOCUMENTS

| WO | 02/059148 | 8/2002 |
|---|---|---|
| WO | 2007/140371 A2 | 6/2007 |
| WO | 2010/087994 A2 | 8/2010 |
| WO | 2010/099536 A2 | 9/2010 |
| WO | 2010/099536 A3 | 9/2010 |
| WO | 2012/145522 | 10/2012 |
| WO | 2013/003555 A1 | 1/2013 |
| WO | 2013/016653 A1 | 1/2013 |
| WO | 2013/1533203 | 10/2013 |
| WO | 2013/177231 | 11/2013 |
| WO | 2014/001324 A1 | 1/2014 |
| WO | 2014/001325 A1 | 1/2014 |
| WO | 2014/055936 | 4/2014 |
| WO | 2014/131906 A1 | 9/2014 |
| WO | 2014/145441 | 9/2014 |
| WO | 2014/177042 | 11/2014 |
| WO | 2014/183066 A2 | 11/2014 |

OTHER PUBLICATIONS

Branden et al., Introduction to Protein Structure, Garland Publishing Inc., New York, p. 247, 1991.*
Sadowski et al., Current Opinion in Structural Biology 19:357-362, 2009.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Antos et al., "Site-Specific N- and C-Terminal Labeling of a Single Polypeptide Using Sortases of Different Specificity" Journal of the American Chemical Society 131:10800-10801 ( 2009).
Clancy et al., "Sortase transpeptidases: Insights into mechanism, substrate specificity, and inhibition" Biopolymers 94(4):385-396 ( 2010).

(Continued)

*Primary Examiner* — Delia M Ramirez
(74) *Attorney, Agent, or Firm* — Nicole Fortune

(57) ABSTRACT

Herein is reported a method for producing an enzymatic conjugation product of three polypeptides comprising the simultaneous incubation of i) a first polypeptide comprising the amino acid sequence LPXTG (SEQ ID NO: 20, wherein X can be any amino acid residue), a second polypeptide comprising the amino acid sequence LPXTA (SEQ ID NO: 31, wherein X can be any amino acid residue), a third polypeptide that has two N-termini whereby the polypeptide has an oligo-glycine $G_m$ (m=2 (SEQ ID NO: 22), or 3 (SEQ ID NO: 23), or 4 (SEQ ID NO: 24), or 5 (SEQ ID NO: 25)) amino acid sequence at its first N-terminus and an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its second N-terminus, a fourth polypeptide with sortase activity whereby the polypeptide is derived from *Staphylococcus aureus* sortase A, and a fifth polypeptide with sortase activity whereby the polypeptide is derived from *Streptococcus pyogenes* sortase A and the recovering of the conjugate from the reaction mixture.

12 Claims, 9 Drawing Sheets

Specification includes a Sequence Listing.

(56) References Cited

OTHER PUBLICATIONS

Li et al., "Irreversible Site-Specific Hydrazinolysis of Proteins by Use of Sortase" Angewandte Chemie International Edition in English 53:2198-2202 ( 2014).

Marraffini et al., "Sortases and the Art of Anchoring Proteins to the Envelopes of Gram-Positive Bacteria" Microbiology and Molecular Biology Reviews 70: 192-221 ( 2006).

Marvin et al., "Recombinant approaches to IgG-like bispecific antibodies" Acta Pharmacologica Sinica 26(6):649-658 (Jun. 2005).

Meissner, P. et al. et al., "Transient gene expression: recombinant protein production with suspension-adapted HEK293-EBNA cells" Biotechnol Bioeng 75:197-203 ( 2001).

Popp et al., "Sortase-catalyzed transformations that improve the properties of cytokines" PNAS 108:3169-3174 ( 2011).

Race et al., "Crystal Structure of*Streptococcus pyogenes*Sortase A" Journal of Biological Chemistry 284:6924-6933 ( 2009).

Ta et al., "Enzymatic Single-Chain Antibody Tagging a Universal Approach to Targeted Molecular Imaging and Cell Homing in Cardiovascular Disease" Circulation Research 109:365-373 ( 2011).

Biswas et al., "Sorting ofLPXTG Peptides by Archetypal Sortase A: Role of Invariant Substrate Residues in Modulating the Enzyme Dynamics and Conformational Signature of a Productive Substrate" Biochemistry 53(15):2515-2524 ( 2014).

International Search Report for PCT/EP2015/079692 dated Mar. 16, 2016.

Levary et al., "Protein-Protein Fusion Catalyzed by Sortase A" PLoS ONE 6(4 Suppl e18342):1-6 (Apr. 2011).

Madej et al., "Engineering of an Anti-Epidermal Growth Factor Receptor Antibody to Single Chain Format and Labeling by Sortase A-Mediated Protein Ligation" Biotechnology and Bioengineering 109(6):1461-1470 (Jun. 2012).

Marraffini et al., "Anchoring of Surface Proteins to the Cell Wall of *Staphylococcus aureus*" Journal of Biological Chemistry 279(36):37763-37770 (Sep. 3, 2004).

Popp et al., "Making and Breaking Peptide Bonds: Protein Engineering Using Sortase" Angew. Chem. Int. Ed. 50:5024-5032 (2011).

Strijbis et al., "Protein Ligation in Living Cells Using Sortase" Traffic 13:780-789 (2012).

Ton-That et al., "Purification and Characterization of Sortase, the Transpeptidase that Cleaves Surface Proteins of *Staphylococcus aureus* at the LPXTG Motif" PNAS 96(22):12424-12429 (Oct. 26, 1999).

Tsukiji et al., "Sortase-Mediated Ligation: A Gift from Gram-Positive Bacteria to Protein Engineering" ChemBioChem 10:787-798 (2009).

Yamamura et al., "Enhancement of Sortase A-Mediated Protein Ligation by Inducing a beta-Hairpin Structure around the Ligation Site" Chem. Commun. 47:4742-4744 (2011).

Frankel et al., "*Staphylococcus aureus* Sortase Transpeptidase SrtA: Insight into the Kinetic Mechanism and Evidence for a Reverse Protonation Catalytic Mechanism" Biochemistry 44(33):11188-11200 ( 2005).

Heck et al., "Continuous Monitoring of Enzymatic Reactions on Surfaces by Real-Time Flow Cytometry: Sortase A Catalyzed Protein Immobilization as a Case Study" Bioconjugate Chemistry 25(8):1492-1500 (2014).

Hess et al., "M13 Bacteriophage Display Framework that Allows Sortase-Mediated Modification of Surface-Accessible Phage Proteins" Bioeonjugate Chemistry 23:1478-1487 ( 2012).

International Search Report of PCT/EP2015/079615 dated Mar. 14, 2016.

Li et al., "A novel reporter system monitoring Sortase A catalyzed protein ligation efficiency" Chinese Journal of Biotechnology 30(2):284-293 (2014).

Matsumoto et al., "Site-Specific Tetrameric Streptavidin-Protein Conjugation Using Sortase A" Journal of Biotechnology 152:37-42 (2011).

Matsumoto et al., "Sortase A-Catalyzed Site-Specific Coimmobilization on Microparticles via Streptavidin" Langmuir 28(7):3553-3557 ( 2012).

Oteng-Pabi et al., "Continuous enzyme-coupled assay for microbial transglutaminase activity" Analytical Biochemistry 441(2):169-173 (2013).

Ton-That et al., "Anchoring of surface proteins to the cell wall of *Staphylococcus aureus*. Sortase catalyzed in vitro transpeptidation reaction using LPXTG peptide and NH(2)-Gly(3) substrates" The Journal of biological chemistry 275(13):9876-81 ( 2000).

Ton-That et al., "Anchoring of Surface Proteins to the Cell Wall of *Staphylococcus aureus*" Journal of Biological Chemistry 277(9):7447-7452 (2002).

NCBI Database, 002984641.1, (sortase SrtA [*Streptococcus pyogenes*]), pp. PN 171203 May 2013.

NCBI Database, 031862293.1, (sortase A [*Staphylococcus aureus*]), pp. PN 171203 Sep. 2014.

Tan et al., "Applications of Transpeptidase Sortase A for Protein Modifications" Progress in Chemistry 26(10):1741-1751 (2014).

Walsh, Christopher Antibiotics: actions, origins, resistance Washington, D.C.:ASM Press, (2003).

Abbot, A., et al., "Processing of Leather Using Deep Eutectic Solvents" ACS Sustainable Chem Eng 3(6):1241-1247 (Apr. 20, 2015).

Clancy et al., "Sortase Transpeptidases: Insights into mechanism, substrate specificity and inhibition" Peptide Science 94(4):385-396 (2010).

Dai, Y et al. Natural Deep Eutectic Solvents and Their Application in Natural Product Research and Development, Dissertation "3" Universiteit Leiden, (Sep. 24, 2013).

Durand et al., "Deep eutectic solvents: Synthesis, application, and focus on lipase-catalyzed reactions" Eur. J. Lipid Sci. Technol. 115:379-385 (2013).

Garcia et al., "Deep Eutectic Solvents: Physicochemical Properties and Gas Separation Applications" Energy & Fuels 29:2616-2644 (2015).

Gaspar, A., et al., "Baccillus anthracis Sortase A (SrtA) Anchors LPXTG Motif-Containing Surface Proteins to the Cell Wall Envelope" J Bacteriol 187(13):4646-4655 (Jul. 1, 2005).

Huang et al., "Deep eutectic solvents can be viable enzyme activators and stabilizers" Journal of Chem. Technol Biotechnol 89:1875-1981 (2014).

ISR and Written Opinion of PCT/EP2016/072512 (dated Nov. 17, 2016).

ISR for PCT/EP2017/052318 (dated May 4, 2017).

ISR of PCT/EP2016/072510 (dated Nov. 15, 2016).

Lindberg et al., "Deep eutectic solvents (DESs) are viable cosolvents for enzyme-catalyzed epoxide hydrolysis" Journal of Biotechnology 147:169-171 (2010).

Ling, J., et al., "Protein Thioester Synthesis Enabled by Sortase" J Am Chem Soc 134(26):10749-10752 (Jun. 11, 2012).

Maugeri et al., "Chymotrypsin-Catalyzed Peptide Synthesis in Deep Eutectic Solvents" European Journal of Organic Chemistry:4223-4228 (2013).

Schmohl, L. et al., "Sortase-mediated ligations for the site-specific modification of proteins" Curr Opin Chem Biol 22:122-128 (Oct. 1, 2014).

Smith, E., et al., "Deep Eutectic Solvents (DESs) and Their Applications" Chem Rev 114(21):11060-11082 (Oct. 10, 2014).

Tang et al., "Recent developments in deep eutectic solvents in chemical sciences" Monatsh Chem. 144:1427-1454 (2013).

Written Opinion for PCT/EP2017/052318.

Zhang et al., "Deep eutectic solvents: syntheses, properties and applications" Chem Soc Rev 41:7108-7146 (2012).

Zhao et al., "Choline-based deep eutectic solvents for enzymatic preparation of biodiesel from soybean oil" Journal of Molecular Catalysis B: Enzymatic 85-86:243-247 (2013).

Zhao et al., "Protease activation in glycerol-based deep eutectic solvents" J Mol Catal B Enzym. 72:163-167 (2011).

Antos, John M., et al. "Supporting Information" Title: Site-specific N- and C-terminal labeling of a single polypeptide using sortases of different specificity, Whitehead Institute for Biomedical Research, 9 Cambridge Center, Cambridge, MA 02142, pp. S1-S20 (2009).

(56) References Cited

OTHER PUBLICATIONS

Garandeau et al., "The Sortase SrtA of Listeria monocytogenes Is Involved in Processing of Internalin and in Virulence" Infection and Immunity:1382-1390 (Mar. 2002).

Guimaraes et al., "Site-specific C-terminal and internal loop labeling of proteins using sortase-mediated reactions" Nature Protocols 8:1787-1799 (2013).

Hongyuan et al., "Sortase-Mediated Protein Ligation: A New Method for Protein Engineering" J. Am. Chem. Soc. 126:2670-2671 (2004).

ISR for PCT/EP2016/072502 (dated Nov. 8, 2016).

Kyoui et al., "Genetic distance in the whole-genome perspective on Listeria monocytogenes strains F2-382 and NIHS-28 that show similar subtyping results" BMC Microbiology 14:309 (2014).

Nguyen et al., "Establishment of an experimental system allowing immobilization of proteins on the surface of Bacillus subtilis cells" Journal of Biotechnology 122:473-482 (2006).

Other Database, Database EBI accession No. UNIPROT:AOAOE1R5I2, (SubName: Full=Putative cysteine protease ywpE {ECO:0000313|EMBL:CCO63533.1}; EC=3.4.22.- {ECO:0000313|EMBL:CCO63533.1};) May 27, 2015.

Other Database, UNIPROT:A0A0B8RCN4,Database accession No. UNIPROT:A0A0B8RCN4 SubName: Full=Cysteine protease {ECO:0000313:EMBL:GAM94542.1}; SubName: Full=Sortase {ECO:00003131EMBL:AGR15336.1}; SubName: Full=Sortase A {ECO:0000313:EMBL:AKK25356.1} Sep. 16, 2015.

Other Database, UNIPROT:A9LY59,retrieved from EBI accession No. UNIPROT:A9LY59, SubName: Full=Sortase A {ECO:0000313:EMBL:ABX11549.1}; Flags: Fragment; Feb. 5, 2008.

Sutherland and Durand, Recent Results Cancer Res 95:24-49 (1984).

Bierne et al., "Inactivation of the srtA gene in Listeria monocytogenes inhibits anchoring of surface proteins and affects virulence" Molecular Microbiology 43(4):869-881 (2002).

Bolken et al., "Inactivation of the srtA gene in *Streptococcus gordonii* inhibits cell wall anchoring of surface proteins and decreases in vitro and in vivo adhesion" Infection and Immunity 69(1):75-80 (2001).

Chan et al., "Covalent attachment of proteins to solid supports and surfaces via sortase-mediated ligation" PlosOne(11):e1164 (2007).

Dhar et al., "Anchor Structure of cell wall surface proteins in listeria monocytogenes" Biochemistry 39(13):3725-3733 (2000).

Fischetti et al., "Conservation of a hexapeptide sequence in the anchor region of surface proteins from Gram-positive cocci" Molecular Microbiology 4(9):1603-1605 (1990).

Glaser et al., "Comparative genomics of listeria species" Science 294:849-852 (2001).

Ilangovan et al., "Structure of sortase, the transpeptidase that anchors proteins to the cell wall of *Staphylococcus aureus*" Proceedings of the National Academy of Sciences 98(11):6056-6061 (2001).

Kruger et al., "Analysis of the substrate specificity of the *Staphylococcus aureus* sortase transpeptidase SrtA" Biochemistry 43(6):1541-1551 (2004).

Mao et al., "Sortase-Mediated protein ligation: A new method for protein engineering" Journal of American Chemical Society 126:2670-2671 (2004).

Mazmanian et al., "Sortase-catalysed anchoring of surface proteins to the cell wall of *Staphlococcus aureus*" Molecular Microbiology 40(5):1049-1057 (2001).

Mazmanian et al., "*Staphylococcus aureus* Sortase, an enzyme that anchors surface proteins to the cell wall" Science 285:760-763 (1999).

Pallen et al., "An embarrassment of sortases—a richness of substrates?" Trends in Microbiology 9(3):97-102 (2001).

Parthasarathy et al., Bioconjugate Chem 18:469-476 (2007).

Samantaray et al., "Peptide-sugar ligation catalyzed by transpeptidase sortase: A facile approach to neoglycoconjugate synthesis" Journal Am. Chem. Soc. 130:2132-2133 (2008).

Dawson et al., "Synthesis of Native Proteins by Chemical Ligation" Annu. Rev. Biochem 69:923-60 (2000).

Jiang et al., "Research Progress on Sortase and its Application in Biotechnology" Current Biotechnology 1(3):184-188 (2011).

Yan et al., "Synthesis of Peptides and Proteins without Cysteine Residues by Native Chemical Ligation Combined with Desulfurization" Journal Am. Chem. Soc. 123:526-533 (2001).

Swee, Lee Kim et al., "Sortase-mediated modification of αDEC205 affords optimization of antigen presentation and immunization against a set of viral epitopes" PNAS 110:1428-1433 (2013).

Tanaka et al., "Sire-Specific Protein Modification on Living Cells Catalyzed by Sortase" ChemBioChem 9:802-807 (2008).

Witte et al., "Preparation of unnatural N-to-N and C-to-C protein fusions" PNAS 109(30):11993-11998 (2012).

\* cited by examiner

ENZYMATIC ONE-POT REACTION FOR DOUBLE POLYPEPTIDE CONJUGATION IN A SINGLE STEP

CROSS REFERENCE TO RELATED APPLICATIONS

This application is a continuation of International Patent Application No. PCT/EP2015/079692 filed Dec. 15, 2015, which claims priority benefit to European Patent Application No. 14198534.1 filed Dec. 17, 2014, each of which are hereby incorporated by reference in their entireties.

SEQUENCE LISTING

The instant application contains a Sequence Listing submitted via EFS-Web and is hereby incorporated by reference in its entirety. Said ASCII copy, created Jul. 13, 2017, is named P32477_US_Substitute_Sequence_Listing.txt, and is 16,026 bytes in size.

Herein is reported a method for the simultaneous enzymatic conjugation of three compounds via peptide bonds.

BACKGROUND OF THE INVENTION

Sortase A (SrtA) is a membrane bound enzyme which attaches proteins covalently to the bacterial cell wall. The specific recognition motif on the SrtA substrate is LPXTG, whereby the enzyme cleaves between the residues threonine and glycine. The recognition motif on the peptidoglycan is a pentaglycine motif. It has been shown that a triglycine and even a diglycine motif on the free N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking the protein substrate to peptidoglycan and regenerating SrtA. SrtA can be used to covalently conjugate chemically synthetized peptides to recombinantly expressed proteins.

Sortase A from *Staphylococcus aureus* is a thiol containing transpeptidase that recognizes an LPXTG motif in multiple structurally unrelated substrates and tolerates C-terminal extensions of the oligoglycine nucleophile, allowing diverse functionalized nucleophiles to be installed site specifically onto proteins equipped with an LPXTG motif (Popp, W. M., et al. Proc. Natl. Acad. Sci. USA 108 (2011) 3169-3174). The related *Streptococcus pyogenes* sortase accepts di-alanine based nucleophiles, which the *S. aureus* enzyme does not. This sortase cleaves the LPXTA motif between threonine and alanine and allows installation of modified alanine-based nucleophiles. SrtA$_{strep}$ also recognizes and cleaves LPXTG motifs, albeit with reduced efficiency, however the LPXTA motif is refractory to cleavage by SrtA$_{staph}$ (Popp et al. supra).

In WO 2010/087994 methods for ligation and uses thereof are reported. Recombinant approaches to IgG-like bispecific antibodies are reported by Marvin, J. S., et al. (Acta Pharmacol. Sinica 26 (2005) 649-658). Levary, D. A., et al. (PLoS one, 6 (2011) e18342.1-e18342.6) report protein-protein fusion catalyzed by sortase A. In WO 2013/003555 the use of sortases to install click chemistry handles for protein ligation is reported.

Strijbis, K. et al (Traffic 13 (2012) 780-789) report protein ligation in living cells using sortase. It has been stated by them that the Ca$^{2+}$-dependent *S. aureus* sortase A is not functional intracellularly, but that the Ca$^{2+}$-independent *S. pyogenes* sortase A is functional in the cytosol and endoplasmic reticulum (ER) lumen of both *Saccharomyces cerevisiae* and mammalian HEK293T cells.

Levary, D. A., et al., report protein-protein fusion catalyzed by Sortase A (PLOS ONE 6 (2011)). Engineering of an anti-epidermal growth factor receptor antibody to single chain format and labeling by sortase A-mediated protein ligation is reported by Madej, M. P., et al. (Biotechnol. Bioeng. 109 (2012) 1461-1470). Ta, H. T., et al., report enzymatic single-chain antibody tagging as a universal approach to targeted molecular imaging and cell homing in cardiovascular diseases (Cir. Res. 109 (2011) 365-373). Popp, M., et al., report making and breaking peptide bonds—protein engineering using sortase (Angew. Chem. Int. Ed. Eng. 50 (2011) 5024-5032). In WO 2010/087994 methods for ligation and uses thereof are reported. Engineered proteins with high affinity for DOTA chelates are reported in WO 2010/099536.

A truncated SrtA, that lacks the N-terminal membrane-anchoring motif, has been used for cell-surface protein labeling, covalent protein immobilization and incorporation of novel functionality into proteins. However, yields of SrtA-mediated ligation are always lower than 70%, if using equimolar amounts of substrate, because the reaction is reversible. Another drawback is the hydrolysis of the reaction intermediate which leads to a LPXT product which is not the intended one. This is especially problematic by long periods of incubation with SrtA. That also means that even small amounts of SrtA left in the final product can destroy it over time; this is a big issue for biologics where quality standards are very high.

Different efforts to block the reverse reactions of Sortase have been reported. Yamamura, Y., et al. (Chem. Commun. 47 (2011) 4742-4744) reported enhancement of sortase A-mediated protein ligation by inducing a beta-hairpin structure around the ligation site by introducing a β-hairpin around the recognition site of the substrate.

Sorting of LPXTG peptides by archetypal sortase A, role of invariant substrate residues in modulating the enzyme dynamics and conformational signature of a productive substrate was reported by Biswas, T., et al. (Biochem. 53 (2014) 2515-2524).

Li, Y. M., et al. report irreversible site-specific hydrazinolysis of proteins by use of Sortase (Angew. Chem. Int. Ed. Engl. 53 (2014) 2198-2202).

In WO 2014/001324 a method for selection and production of tailor-made highly selective and multi-specific targeting entities containing at least two different binding entities and uses thereof is reported. Marraffini, L. A., et al. (J. Biol. Chem. 279 (2004) 37763-37770) report for anchoring of surface proteins to the cell wall of *Staphylococcus aureus* a conserved arginine residue is required for efficient catalysis of Sortase A.

SUMMARY OF THE INVENTION

It has been found that two peptide bonds can be formed in an enzymatic one-pot reaction by simultaneous incubation with a first sortase originating from *Staphylococcus aureus* and a second sortase originating from *Streptococcus pyogenes*. The first sortase is specific for the combination of i) the sortase amino acid motif LPXTG (SEQ ID NO: 20, wherein X can be any amino acid residue) and ii) an oligo-glycine as nucleophile (SEQ ID NO: 22 to 25), whereas the second sortase is specific for the combination of i) the sortase amino acid motif LPXTA (SEQ ID NO: 31, wherein X can be any amino acid residue) and ii) an oligo-alanine (SEQ ID NO: 26 to 29) as nucleophile. As these two sortases have orthogonal specificities two transpeptidation reactions can be performed simultaneously as enzymatic one-pot reaction.

Thus, one aspect as reported herein is a method for producing an enzymatic conjugation product of three polypeptides comprising the following steps
incubating simultaneously
a) i) a first polypeptide comprising the amino acid sequence LPXTG (SEQ ID NO: 20, wherein X can be any amino acid residue),
ii) a second polypeptide comprising the amino acid sequence LPXTA (SEQ ID NO: 31, wherein X can be any amino acid residue),
iii) a third polypeptide that has two N-termini whereby the polypeptide has an oligo-glycine $G_m$ (m=2 (SEQ ID NO: 22), or 3 (SEQ ID NO: 23), or 4 (SEQ ID NO: 24), or 5 (SEQ ID NO: 25)) amino acid sequence at its first N-terminus and an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its second N-terminus,
iv) a fourth polypeptide with sortase activity whereby the polypeptide is derived from *Staphylococcus aureus* sortase A, and
v) a fifth polypeptide with sortase activity whereby the polypeptide is derived from *Streptococcus pyogenes* sortase A,
or
b) i) a first polypeptide comprising the amino acid sequence LPXTG (SEQ ID NO: 20, wherein X can be any amino acid residue),
ii) a second polypeptide that has an oligo-glycine $G_m$ (m=2 (SEQ ID NO: 22), or 3 (SEQ ID NO: 23), or 4 (SEQ ID NO: 24), or 5 (SEQ ID NO: 25)) amino acid sequence at its N-terminus and that comprises the amino acid sequence LPXTA (SEQ ID NO: 31, wherein X can be any amino acid residue),
iii) a third polypeptide that has an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its N-terminus,
iv) a fourth polypeptide with sortase activity whereby the polypeptide is derived from *Staphylococcus aureus* sortase A, and
v) a fifth polypeptide with sortase activity whereby the polypeptide is derived from *Streptococcus pyogenes* sortase A,
or
c) i) a first polypeptide comprising the amino acid sequence LPXTA (SEQ ID NO: 31, wherein X can be any amino acid residue),
ii) a second polypeptide that has an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its N-terminus and that comprises the amino acid sequence LPXTG (SEQ ID NO: 20, wherein X can be any amino acid residue),
iii) a third polypeptide that has an oligo-glycine $G_m$ (m=2 (SEQ ID NO: 22), or 3 (SEQ ID NO: 23), or 4 (SEQ ID NO: 24), or 5 (SEQ ID NO: 25)) amino acid sequence at its N-terminus,
iv) a fourth polypeptide with sortase activity whereby the polypeptide is derived from *Staphylococcus aureus* sortase A, and
v) a fifth polypeptide with sortase activity whereby the polypeptide is derived from *Streptococcus pyogenes* sortase A,
and
recovering the conjugate from the reaction mixture and thereby producing the enzymatic conjugation product of three polypeptides.

In one embodiment the first, second and third polypeptides are present at about equimolar concentration.

In one embodiment the oligo-alanine is a di-alanine (SEQ ID NO: 26) or a tri-alanine (SEQ ID NO: 27).

In one embodiment the oligo-glycine is a di-glycine (SEQ ID NO: 22) or a tri-glycine (SEQ ID NO: 23).

In one embodiment the fourth polypeptide has the amino acid sequence of SEQ ID NO: 21.

In one embodiment the fifth amino acid sequence has the amino acid sequence of SEQ ID NO: 34.

In one embodiment the first polypeptide, the second polypeptide and the third polypeptide are independently of each other selected from an antibody variable domain, an antibody heavy chain Fab-fragment, an antibody Fc-region, and a tag.

In one embodiment the method further comprises the step of purifying the enzymatic conjugation product of three polypeptides.

In one embodiment the amino acid sequence LPXTG (SEQ ID NO: 20, wherein X can be any amino acid residue) and/or the amino acid sequence LPXTA (SEQ ID NO: 31, wherein X can be any amino acid residue) is followed by at least one amino acid residue.

DETAILED DESCRIPTION OF THE INVENTION

I. Definitions

In the present specification and claims the numbering of the residues in an immunoglobulin heavy chain Fc-region is that of the EU index of Kabat (Kabat, E. A., et al., Sequences of Proteins of Immunological Interest, 5th ed., Public Health Service, National Institutes of Health, Bethesda, Md. (1991), NIH Publication 91-3242, expressly incorporated herein by reference).

The term "alteration" denotes the mutation, addition, or deletion of one or more amino acid residues in a parent amino acid sequence, e.g. of an antibody or fusion polypeptide comprising at least an FcRn binding portion of an Fc-region, to obtain a variant antibody or fusion polypeptide.

The term "amino acid mutation" denotes a modification in the amino acid sequence of a parent amino acid sequence. Exemplary modifications include amino acid substitutions, insertions, and/or deletions. In one embodiment the amino acid mutation is a substitution. The term "amino acid mutations at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring or non-proteinogenic amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, aib and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "amino acid insertion" denotes the incorporation of at least one additional amino acid residue into a predetermined parent amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as defined above.

The term "amino acid deletion" denotes the removal of at least one amino acid residue at a predetermined position in an amino acid sequence.

Within this application whenever an amino acid alteration is mentioned it is a deliberated amino acid alteration and not a random amino acid modification.

The term "tag" denotes a sequence of amino acid residues connected to each other via peptide bonds that has specific binding properties. In one embodiment the tag is an affinity or purification tag. In one embodiment the tag is selected from Arg-tag, His-tag, Flag-tag, 3×Flag-tag, Strep-tag, Nano-tag, SBP-tag, c-myc-tag, S-tag, calmodulin-binding-peptide, cellulose-binding-domain, chitin-binding-domain, GST-tag, or MBP-tag. In one embodiment the tag is selected from SEQ ID NO: 01 (RRRRR), or SEQ ID NO: 02 (RRRRRR), or SEQ ID NO: 03 (HHHHHH), or SEQ ID NO: 04 (KDHLIHNVHKEFHAHAHNK), or SEQ ID NO: 05 (DYKDDDDK), or SEQ ID NO: 06 (DYKDHDGDYKDHDIDYKDDDDK), or SEQ ID NO: 07 (AWRHPQFGG), or SEQ ID NO: 08 (WSHPQFEK), or SEQ ID NO: 09 (MDVEAWLGAR), or SEQ ID NO: 10 (MDVEAWLGARVPLVET), or SEQ ID NO: 11 (MDEKTTGWRGGHVVEGLAGELEQLRAR-LEHHPQGQREP), or SEQ ID NO: 12 (EQKLISEEDL), or SEQ ID NO: 13 (KETAAAKFERQHMDS), or SEQ ID NO: 14 (KRRWKKNFIAVSAANRFKKISSSGAL), or SEQ ID NO: 15 (cellulose binding domain), or SEQ ID NO: 16 (cellulose binding domain), or SEQ ID NO: 17 (TNPGV-SAWQVNTAYTAGQLVTYNGKTYKCLQPHT-SLAGWEP SNVPALWQLQ), or SEQ ID NO: 18 (GST-tag), or SEQ ID NO: 19 (MBP-tag), or SEQ ID NO: 35 (C-tag).

An "effective amount" of an agent, e.g., a pharmaceutical formulation, refers to an amount effective, at dosages and for periods of time necessary, to achieve the desired therapeutic or prophylactic result.

The term "individual" or "subject" denotes a mammal. Mammals include, but are not limited to, domesticated animals (e.g. cows, sheep, cats, dogs, and horses), primates (e.g., humans and non-human primates such as monkeys), rabbits, and rodents (e.g., mice, rats, and hamsters). In certain embodiments, the individual or subject is a human.

The term "pharmaceutical formulation" refers to a preparation which is in such a form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "position" denotes the location of an amino acid residue in the amino acid sequence of a polypeptide. Positions may be numbered sequentially, or according to an established format, for example the EU index of Kabat for antibody numbering.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

II. Enzymatic Conjugation Using Sortase A

A covalent conjugate comprising two in vivo not covalently associated entities can be obtained in vitro by using the enzyme sortase, especially sortase A.

Sortase A (SrtA) is a membrane bound enzyme which attaches proteins covalently to the bacterial cell wall. The specific recognition motif on the SrtA substrate is LPXTG, whereby the enzyme cleaves between the residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking the protein substrate to peptidoglycan and regenerating SrtA. SrtA can be used to covalently conjugate chemically synthetized peptides to recombinantly expressed proteins.

Many gram-positive bacteria use sortase to covalently anchor a variety of surface proteins including virulence factors to their cell wall (peptidoglycan). Sortases are membrane associated enzymes. The wild-type *Staphylococcus aureus* sortase A (SrtA) is a polypeptide of 206 amino acids with an N-terminal membrane-spanning region. In a first step, sortase A recognizes substrate proteins that contain a LPXTG (SEQ ID NO: 20) amino acid sequence motif and cleaves the amide bond between the Thr and Gly by means of an active-site Cys. This peptide cleaving reaction results in a sortase A-substrate thioester intermediate. In a second step the thioester acyl-enzyme intermediate is resolved by nucleophilic attack of an (the N-terminal) amino group of an oligoglycine containing second substrate polypeptide (corresponding to the pentaglycine unit of peptidoglycan in *S. aureus*) leading to a covalently linked cell wall protein and the regeneration of sortase A. In the absence of oligoglycine nucleophiles, the acyl-enzyme intermediate can be hydrolyzed by a water molecule.

Sortase-mediated ligation/conjugation has begun to be applied for a variety of protein engineering and bioconjugation purposes. This technique enables the introduction of natural and synthetic functionalities into LPXTG-tagged recombinant or chemically synthesized polypeptides. Examples include the covalent attachment of oligoglycine derivatized polymers (e.g. PEG), fluorophores, vitamins (e.g. biotin and folate), lipids, carbohydrates, nucleic acids, synthetic peptides and proteins (e.g. GFP) (see e.g. Tsukiji, S. and Nagamune, T., ChemBioChem 10 (2009) 787-798; Popp, M. W. L. and Ploegh, H. L., Angew. Chem. Int. Ed. Engl. 50 (2011) 5024-5032).

For the enzymatic conjugation a soluble truncated sortase A lacking the membrane-spanning region (SrtA; amino acid residues 60-206 of *Staphylococcus aureus* SrtA) can be used (SEQ ID NO: 21; see also Ton-That, H., et al., Proc. Natl. Acad. Sci. USA 96 (1999) 12424-12429; Ilangovan, H., et al., Proc. Natl. Acad. Sci. USA 98 (2001) 6056-6061).

III. Recombinant Methods

Any polypeptide domain (e.g. a single chain antigen binding polypeptide such as a scFv, a scFab, or a darpin, or a multi chain antigen binding polypeptide such as a dsFv or a Fab) comprising an oligoglycine motif at its N-terminus (GG (SEQ ID NO: 22), GGG (SEQ ID NO: 23), GGGG (SEQ ID NO: 24), GGGGG (SEQ ID NO: 25)) can be expressed and purified from the supernatant of eukaryotic cells (e.g. HEK293 cells, CHO cells). It does not matter if the polypeptide is an isolated polypeptide or comprised in a multimeric or heteromeric entity.

Suitable host cells for cloning or expression/secretion of polypeptide-encoding vectors include prokaryotic or eukaryotic cells described herein. For example, polypeptides may be produced in bacteria, in particular when glycosylation is not needed (see, e.g., U.S. Pat. Nos. 5,648,237, 5,789,199 and 5,840,523, Charlton, Methods in Molecular Biology 248 (2003) 245-254 (B. K. C. Lo, (ed.), Humana Press, Totowa, N.J.), describing expression of antibody fragments in *E. coli*). After expression, the polypeptide may be isolated from the bacterial cell paste in a soluble fraction or may be isolated from the insoluble fraction so called inclusion bodies which can be solubilized and refolded to bioactive forms. Thereafter the polypeptide can be further purified.

In addition to prokaryotes, eukaryotic microbes such as filamentous fungi or yeasts are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gerngross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. Nos. 5,959,177, 6,040,498, 6,420,548, 7,125,978 and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are the COS-7 cell line (monkey kidney CV1 cell transformed by SV40); the HEK293 cell line (human embryonic kidney); the BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line (e.g. described in Mather, et al., Anal. N.Y. Acad. Sci. 383 (1982) 44-68); the MRC5 cell line; and the FS4 cells-line. Other useful mammalian host cell lines include the CHO cell line (Chinese hamster ovary cell), including DHFR negative CHO cell lines (see e.g. Urlaub, et al., Proc. Natl. Acad. Sci. USA 77 (1980) 4216), and myeloma cell lines such as Y0, NS0 and Sp2/0 cell line. For a review of certain mammalian host cell lines suitable for polypeptide production, see, e.g., Yazaki, and Wu, Methods in Molecular Biology, Antibody Engineering 248 (2004) 255-268 (B. K. C. Lo, (ed.), Humana Press, Totowa, N.J.).

IV. The Method as Reported Herein

It has been found that two peptide bonds can be formed in an enzymatic one-pot reaction by simultaneous incubation with a first sortase originating from *Staphylococcus aureus* and a second sortase originating from *Streptococcus pyogenes*. The first sortase is specific for the combination of i) the sortase amino acid motif LPXTG (SEQ ID NO: 20, wherein X can be any amino acid residue) and ii) an oligo-glycine as nucleophile (SEQ ID NO: 22 to 25), whereas the second sortase is specific for the combination of i) the sortase amino acid motif LPXTA (SEQ ID NO: 31, wherein X can be any amino acid residue) and ii) an oligo-alanine (SEQ ID NO: 26 to 29) as nucleophile. As these two sortases have orthogonal specificities two transpeptidation reactions can be performed simultaneously as enzymatic one-pot reaction.

Thus, one aspect as reported herein is a method for producing an enzymatic conjugation product of three polypeptides comprising the following steps
  incubating simultaneously
    a) i) a first polypeptide comprising the amino acid sequence LPXTG (SEQ ID NO: 20, wherein X can be any amino acid residue),
    ii) a second polypeptide comprising the amino acid sequence LPXTA (SEQ ID NO: 31, wherein X can be any amino acid residue), iii) a third polypeptide that has two N-termini whereby the polypeptide has an oligo-glycine $G_m$ (m=2 (SEQ ID NO: 22), or 3 (SEQ ID NO: 23), or 4 (SEQ ID NO: 24), or 5 (SEQ ID NO: 25)) amino acid sequence at its first N-terminus and an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its second N-terminus, iv) a fourth polypeptide with sortase activity whereby the polypeptide is derived from *Staphylococcus aureus* sortase A, and v) a fifth polypeptide with sortase activity whereby the polypeptide is derived from *Streptococcus pyogenes* sortase A, or b) i) a first polypeptide comprising the amino acid sequence LPXTG (SEQ ID NO: 20, wherein X can be any amino acid residue), ii) a second polypeptide that has an oligo-glycine $G_m$ (m=2 (SEQ ID NO: 22), or 3 (SEQ ID NO: 23), or 4 (SEQ ID NO: 24), or 5 (SEQ ID NO: 25)) amino acid sequence at its N-terminus and that comprises the amino acid sequence LPXTA (SEQ ID NO: 31, wherein X can be any amino acid residue), iii) a third polypeptide that has an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its N-terminus, iv) a fourth polypeptide with sortase activity whereby the polypeptide is derived from *Staphylococcus aureus* sortase A, and v) a fifth polypeptide with sortase activity whereby the polypeptide is derived from *Streptococcus pyogenes* sortase A, or c) i) a first polypeptide comprising the amino acid sequence LPXTA (SEQ ID NO: 31, wherein X can be any amino acid residue), ii) a second polypeptide that has an oligo-alanine $A_m$ (m=2 (SEQ ID NO: 26), or 3 (SEQ ID NO: 27), or 4 (SEQ ID NO: 28), or 5 (SEQ ID NO: 29)) amino acid sequence at its N-terminus and that comprises the amino acid sequence LPXTG (SEQ ID NO: 20, wherein X can be any amino acid residue), iii) a third polypeptide that has an oligo-glycine $G_m$ (m=2 (SEQ ID NO: 22), or 3 (SEQ ID NO: 23), or 4 (SEQ ID NO: 24), or 5 (SEQ ID NO: 25)) amino acid sequence at its N-terminus, iv) a fourth polypeptide with sortase activity whereby the polypeptide is derived from *Staphylococcus aureus* sortase A, and v) a fifth polypeptide with sortase activity whereby the polypeptide is derived from *Streptococcus pyogenes* sortase A, and recovering the conjugate from the reaction mixture and thereby producing the enzymatic conjugation product of three polypeptides.

The first, second and third polypeptide can independently of each other comprise one or more non-sortase motif moiety. These can be connected either directly or via a linker with the sortase amino acid sequence motif.

Non-Sortase Motif Moiety

The sortase motif amino acid sequence LPXTG may be conjugated, if it is not directly comprised in one of these molecules, to a therapeutic agent (drug), a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label, a tag, or a clearance-modifying agent such as various isomers of polyethylene glycol, a peptide that binds to a third component, or another carbohydrate or lipophilic agent. The conjugation can be either directly or via an intervening linker.

a) Therapeutic Moieties

The drug moiety can be any compound, moiety or group which has a therapeutic effect, such as an antibody, a cytotoxic or cytostatic compound.

A number of therapeutic antibodies directed against cell surface molecules and their ligands are known, such as Rituxan/MabThera/Rituximab, 2H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab (α4-subunit of α4β1 and α4β7 integrins), ReoPro/Abciximab (gpIIb-gpIIa and αvβ3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAMS/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin(SGN-35)/Brentuximab (CD30), and ARH460-16-2 (CD44).

The conjugates obtained with the method as reported herein can be used in the preparation of medicaments for the treatment of e.g. an oncologic disease, a cardiovascular disease, an infectious disease, an inflammatory disease, an autoimmune disease, a metabolic (e.g., endocrine) disease, or a neurological (e.g. neurodegenerative) disease. Exemplary non-limiting examples of these diseases are Alzheimer's disease, non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macrogulbulinemia, carcinomas (such as carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes), melanomas, sarcomas, gliomas, and skin cancers, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

A number of cell surface markers and their ligands are known. For example cancer cells have been reported to express at least one of the following cell surface markers and or ligands, including but not limited to, carbonic anhydrase IX, alpha-fetoprotein, alpha-actinin-4, A3 (antigen specific for A33 antibody), ART-4, B7, Ba-733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, HIF-1-alpha, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, GROB, HLA-DR, HM1.24, human chorionic gonadotropin (HCG) and its subunits, HER2/neu, HMGB-1, hypoxia inducible factor (HIF-1), HSP70-2M, HST-2 or 1a, IGF-1R, IFN-gamma, IFN-alpha, IFN-beta, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, placental growth factor, p53, PLAGL2, prostatic acid phosphatase, PSA, PRAME, PSMA, P1GF, ILGF, ILGF-1R, IL-6, IL-25, RSS, RANTES, T101, SAGE, S100, survivin, survivin-2B, TAC, TAG-72, tenascin, TRAIL receptors, TNF-alpha, Tn-antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi, et al., Clin. Cancer Res. 12 (2006) 5023-5032; Parmiani, et al, J. Immunol. 178 (2007) 1975-1979; Novellino, et al., Cancer Immunol. Immunother. 54 (2005) 187-207).

Thus, antibodies recognizing specific cell surface receptors including their ligands can be used for specific and selective targeting and binding to a number/multitude of cell surface markers that are associated with a disease. A cell surface marker is a polypeptide located on the surface of a cell (e.g. a disease-related cell) that is e.g. associated with signaling event or ligand binding.

In one embodiment, for the treatment of cancer/tumors multispecific binding molecules/bispecific antibodies are produced that target tumor-associated antigens, such as those reported in Herberman, "Immunodiagnosis of Cancer", in Fleisher (ed.), "The Clinical Biochemistry of Cancer", page 347 (American Association of Clinical Chemists (1979)) and in U.S. Pat. No. 4,150,149; 4,361,544; and 4,444,744.

Reports on tumor associated antigens (TAAs) include Mizukami, et al., (Nature Med. 11 (2005) 992-997); Hatfield, et al., (Curr. Cancer Drug Targets 5 (2005) 229-248); Vallbohmer, et al., (J Clin. Oncol. 23 (2005) 3536-3544); and Ren, et al., (Ann. Surg. 242 (2005) 55-63), each incorporated herein by reference with respect to the TAAs identified.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD54, CD67, CD74, CD79a, CD80, CD126, CD138, CD154, CXCR4, B7, MUC1 or 1a, HM1.24, HLA-DR, tenascin, VEGF, P1GF, ED-B fibronectin, an oncogene, an oncogene product (e.g., c-met or PLAGL2), CD66a-d, necrosis antigens, IL-2, T101, TAG, IL-6, MIF, TRAIL-R1 (DR4) and TRAIL-R2 (DR5).

A number of bispecific antibodies are known directed against two different targets, such as BCMA/CD3, different antigens of the HER family in combination (EGFR, HER2, HER3), CD19/CD3, IL17RA/IL7R, IL-6/IL-23, IL-1-beta/IL-8, IL-6 or IL-6R/IL-21 or IL-21R, first specificity directed to a glycoepitope of an antigen selected from the group consisting of Lewis x-, Lewis b- and Lewis y-structures, Globo H-structures, KH1, Tn-antigen, TF-antigen and carbohydrate structures of Mucins, CD44, glycolipids and glycosphingolipids, such as Gg3, Gb3, GD3, GD2, Gb5, Gm1, Gm2, sialyltetraosylceramide and a second specificity directed to an ErbB receptor tyrosine kinase selected from the group consisting of EGFR, HER2, HER3 and HER4, GD2 in combination with a second antigen binding site is associated with an immunological cell chosen from the group consisting of T-lymphocytes NK cell, B-lymphocytes, dendritic cells, monocytes, macrophages, neutrophils, mesenchymal stem cells, neural stem cells, ANG2/VEGF, VEGF/PDGFR-beta, Vascular Endothelial Growth Factor (VEGF) acceptor 2/CD3, PSMA/CD3, EPCAM/CD3, combinations of an antigen is selected from a group consisting of VEGFR-1, VEGFR-2, VEGFR-3, FLT3, c-FMS/CSF1R, RET, c-Met, EGFR, Her2/neu, HER3, HER4, IGFR, PDGFR, c-KIT, BCR, integrin and MMPs with a water-soluble ligand is selected from the group consisting of VEGF, EGF, PIGF, PDGF, HGF, and angiopoietin, ERBB-3/C-MET, ERBB-2/C-MET, EGF receptor 1/CD3, EGFR/HER3, PSCA/CD3, C-MET/CD3, ENDOSIALIN/CD3, EPCAM/CD3, IGF-1R/CD3, FAPALPHA/CD3, EGFR/IGF-1R, IL 17A/F, EGF receptor 1/CD3, and CD19/CD16.

Toxic drug moieties include: (i) chemotherapeutic agents, which may function as microtubule inhibitors, mitosis inhibitors, topoisomerase inhibitors, or DNA intercalators; (ii) protein toxins, which may function enzymatically; and (iii) radioisotopes.

Exemplary toxic drug moieties include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-5), *Momordica charantia* inhibitor, curcin, crotin, *Sapaonaria officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope or other labels may be incorporated in known ways (Fraker et al (1978) Biochem. Biophys. Res.

Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

b) Labels

The non-sortase motif moiety can be a label. Any label moiety which can be covalently attached to the sortase amino acid sequence can be used (see e.g. Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Conjugates comprising a haptenylated label as reported herein may be useful in diagnostic assays, e.g., for detecting expression of an antigen of interest in specific cells, tissues, or serum. For diagnostic applications, a bispecific antibody will be used wherein the first binding specificity binds to a target and the second binding specificity binds to a haptenylated label. The hapten will typically be labeled with a detectable moiety. Numerous labels are available which can be generally grouped into the following categories:

(a) Radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi. Radioisotope labeled conjugates are useful in receptor targeted imaging experiments. The antigen (hapten) can be labeled with ligand reagents that bind, chelate or otherwise complex a radioisotope metal using the techniques described in Current Protocols in Immunology, (1991) Volumes 1 and 2, Coligen et al, Ed. Wiley-Interscience, New York, N.Y., Pubs. Chelating ligands which may complex a metal ion include DOTA, DOTP, DOTMA, DTPA and TETA (Macrocyclics, Dallas, Tex.). Radionuclides can be targeted via complexation with the complex as reported herein (Wu et al, Nature Biotechnology 23(9) (2005) 1137-1146). Receptor target imaging with radionuclide labeled complexes can provide a marker of pathway activation by detection and quantification of progressive accumulation of complexes or corresponding therapeutic antibodies in tumor tissue (Albert et al (1998) Bioorg. Med. Chem. Lett. 8:1207-1210).

Metal-chelate complexes suitable as labels for imaging experiments (US 2010/0111856; U.S. Pat. No. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherpy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to the antigen (hapten) using the techniques disclosed in Current Protocols in Immunology, supra, for example. Fluorescent dyes and fluorescent label reagents include those which are commercially available from Invitrogen/Molecular Probes (Eugene, Oreg., USA) and Pierce Biotechnology, Inc. (Rockford, Ill.).

Detection labels such as fluorescent dyes and chemiluminescent dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling, especially with the following properties: (i) the labeled conjugate should produce a very high signal with low background so that small quantities of conjugate can be sensitively detected in both cell-free and cell-based assays; and (ii) the labeled conjugate should be photostable so that the fluorescent signal may be observed, monitored and recorded without significant photo bleaching. For applications involving cell surface binding of labeled conjugates to membranes or cell surfaces, especially live cells, the labels should (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Techniques for conjugating enzymes to polypeptides are described in O'Sullivan et al "Methods for the Preparation of Enzyme-Antibody Conjugates for use in Enzyme Immunoassay", in Methods in Enzym. (ed. by J. Langone & I T Van Vunakis), Academic Press, New York, 73 (1981) 147-166.

Examples of enzyme-substrate combinations (U.S. Pat. No. 4,275,149; 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

The labeled conjugate as reported herein may be employed in any known assay method, such as ELISA, competitive binding assays, direct and indirect sandwich assays, and immunoprecipitation assays (Zola, Monoclonal Antibodies: A Manual of Techniques (1987) pp. 147-158, CRC Press, Inc.).

Labeled conjugates as reported herein are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al Nuclear Medicine and Biology, 37(3) (2010) 289-297; Chen et al, Bioconjugate Chem. 15 (2004) 41-49; US 2010/0111856 (v) bioluminescence; (vi) fluorescence; and (vii) ultrasound.

Immunoscintigraphy is an imaging procedure in which conjugates labeled with radioactive substances are administered to an animal or human patient and a picture is taken of sites in the body where the conjugate localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 markers are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labeling methods are well known. See Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGruyter, Berlin and New York; and Wong (1991) Chemistry of Protein Conjugation and Cross-linking, CRC Press, Boca Raton, Fla.); DeLeon-Rodriguez et al, Chem. Eur. J. 10 (2004) 1149-1155; Lewis et al, Bioconjugate Chem. 12 (2001) 320-324; Li et al, Bioconjugate Chem. 13 (2002) 110-115; Mier et al Bioconjugate Chem. 16 (2005) 240-237.

Linker

The term "linker" denotes a bifunctional or multifunctional moiety which can be used to conjugate (link) a first moiety with a second moiety. Linked conjugates can be conveniently prepared using a linker having two reactive functionalities.

In one embodiment, a linker has a reactive site which has an electrophilic group that is reactive to a nucleophilic group present in the sortase amino acid sequence. Useful electrophilic groups include, but are not limited to, another thiol, maleimide and haloacetamide groups (see e.g. conjugation method at page 766 of Klussman et al, Bioconjugate Chemistry 15(4) (2004) 765-773).

Examples of thiol-reaction functional groups include, but are not limited to, thiol, maleimide, alpha-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates.

The linker may comprise amino acid residues which link the sortase amino acid sequence to the non-sortase motif moiety. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as non-naturally occurring amino acid analogs, such as e.g. citrulline or β-amino acids, such as e.g. β-alanine, or ω-amino acids such as 4-aminobutyric acid.

In another embodiment, the linker has a reactive functional group which has a nucleophilic group that is reactive to an electrophilic group present in the sortase amino acid sequence. Useful electrophilic groups include, but are not limited to, aldehyde and ketone carbonyl groups. The heteroatom of a nucleophilic group of a linker can react with an electrophilic group in the sortase amino acid sequence and form a covalent bond to the sortase amino acid sequence. Useful nucleophilic groups on a linker include, but are not limited to, hydrazide, oxime, amino, hydrazine, thiosemicarbazone, hydrazine carboxylate, and arylhydrazide. The electrophilic group on an antigen (hapten) provides a convenient site for attachment to a linker.

Typically, peptide-type linkers can be prepared by forming a peptide bond between two or more amino acids and/or peptide fragments. Such peptide bonds can be prepared, for example, according to the liquid phase synthesis method (E. Schroder and K. Lubke "The Peptides", volume 1 (1965) 76-136, Academic Press) which is well known in the field of peptide chemistry.

In another embodiment, the linker may be substituted with groups which modulated solubility or reactivity. For example, a charged substituent such as sulfonate ($SO_3^-$) or ammonium or a polymer such as PEG, may increase water solubility of the reagent and facilitate the coupling reaction of the linker reagent with the antigen (hapten) or the drug moiety, or facilitate the coupling reaction depending on the synthetic route employed.

The conjugates comprising a non-sortase motif moiety as reported herein expressly contemplate, but are not limited to, complexes prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate), and including bis-maleimide reagents: DTME, BMB, BMDB, BMH, BMOE, BM(PEO)$_3$, and BM(PEO)$_4$, which are commercially available from Pierce Biotechnology, Inc. Bis-maleimide reagents allow the attachment of e.g. a thiol group to a thiol-containing drug moiety, label, or linker intermediate, in a sequential or concurrent fashion. Other functional groups besides maleimide, which are reactive with e.g. a thiol group, include iodoacetamide, bromoacetamide, vinyl pyridine, disulfide, pyridyl disulfide, isocyanate, and isothiocyanate.

Exemplary linker include a valine-citrulline (val-cit or vc) dipeptide linker reagent having a maleimide stretcher and a para-aminobenzylcarbamoyl (PAB) self-immolative spacer, and a phe-lys(Mtr) dipeptide linker reagent having a maleimide Stretcher unit and a p-amino benzyl self-immolative spacer.

Cysteine thiol groups are nucleophilic and capable of reacting to form covalent bonds with electrophilic groups on linker reagents and the non-sortase motif moiety or the sortase amino acid sequence including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a haptenylated compound include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Figure 1A:
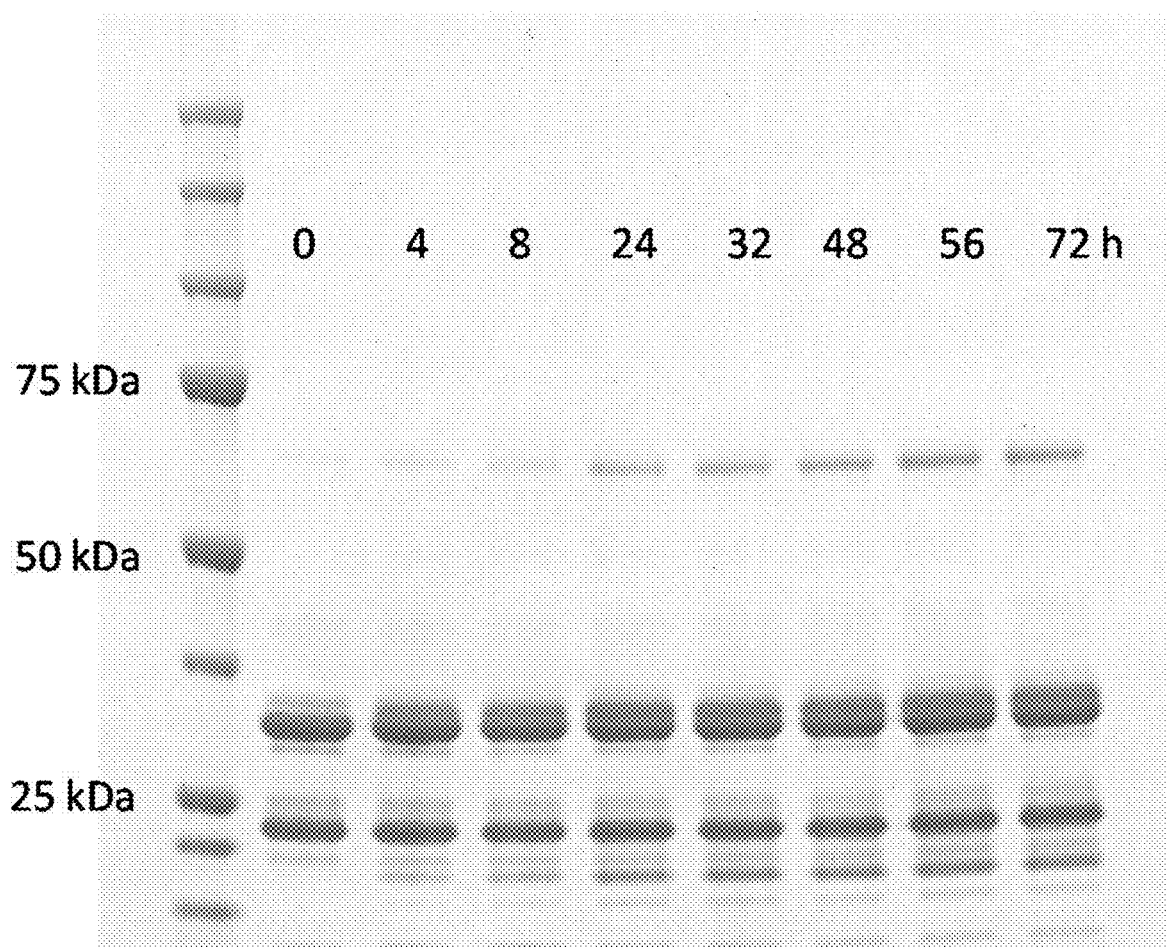
FIG. 1 (A) to (H): SDS-PAGE analysis of experiments 1 to 8 of Example 3.

The following examples, figures and sequences are provided to aid the understanding of the present invention, the true scope of which is set forth in the appended claims. It is understood that modifications can be made in the procedures set forth without departing from the spirit of the invention.

Although the foregoing invention has been described in some detail by way of illustration and example for purposes of clarity of understanding, the descriptions and examples should not be construed as limiting the scope of the invention.

EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany)

Description of the Basic/Standard Mammalian Expression Plasmid

For the expression of a desired gene/protein (e.g. full length antibody heavy chain, full length antibody light chain, or an Fc-chain containing an oligoglycine at its N-terminus) a transcription unit comprising the following functional elements is used:

the immediate early enhancer and promoter from the human cytomegalovirus (P-CMV) including intron A, a human heavy chain immunoglobulin 5'-untranslated region (5'UTR), a murine immunoglobulin heavy chain signal sequence, a gene/protein to be expressed (e.g. full length antibody heavy chain), and the bovine growth hormone polyadenylation sequence (BGH pA).

Beside the expression unit/cassette including the desired gene to be expressed the basic/standard mammalian expression plasmid contains an origin of replication from the vector pUC18 which allows replication of this plasmid in *E. coli*, and a beta-lactamase gene which confers ampicillin resistance in *E. coli*.

Protein Determination

The protein concentration of purified polypeptides was determined by determining the optical density (OD) at 280 nm, using the molar extinction coefficient calculated on the basis of the amino acid sequence of the polypeptide.

Example 1

Generation of an Expression Plasmid for Soluble *S. aureus* Sortase A

The sortase gene encodes an N-terminally truncated *Staphylococcus aureus* sortase A molecule (amino acid sequence of SEQ ID NO: 21).

The expression plasmid for the expression of soluble sortase in *E. coli* cells comprised besides the soluble sortase expression cassette an origin of replication from the vector pUC18, which allows replication of this plasmid in *E. coli*, and the URA3 gene as selectable marker, and the Lad gene to allow induction of transcription using IPTG.

The transcription unit of the soluble sortase comprised the following functional elements:

a T5 promoter, a purification tag, an N-terminally truncated *S. aureus* sortase A encoding nucleic acid, and the To and fd termination sequences.

The amino acid sequence of the mature soluble sortase A derived from *Staphylococcus aureus* is (SEQ ID NO: 21)
QAKPQIPKDKSKVAGYIEIPDADIKEPVYPGPATPEQLNRGVSFAEEN

ESLDDQNISIAGHTFIDRPNYQFTNLKAAKKGSMVYFKVGNETRKYKM

TSIRDVKPTDVGVLDEQKGKDKQLTLITCDDYNEKTGVWEKRKIFVAT

EVK.

The amino acid sequence of the mature soluble sortase A derived from *Streptococcus pyogenes* is (SEQ ID NO: 34)
VLQAQMAAQQLPVIGGIAIPELGINLPIFKGLGNTELIYGAGTMKEEQ

VMGGENNYSLASHHIFGITGSSQMLFSPLERAQNGMSIYLTDKEKIYE

YIIKDVFTVAPERVDVIDDTAGLKEVTLVTCTDIEATERIIVKGELKT

EYDFDKAPADVLKAFNHSYNQVST.

The purification tag has the amino acid sequence MRGSHHHHHHGS (SEQ ID NO: 36).

Example 2

Expression and Analytical Characterization of Sortase

The recombinant production of soluble Sortase was performed by growing *E. coli* cells transformed with the respective Sortase expression plasmids to an OD578 of approx. 0.9 at 37° C. (pre-culture). At this OD578 of approx. 0.9 protein expression was induced by adding 2 mM IPTG and growing the cells for an additional 24 hours at 28° C. Thereafter, cells were harvested by centrifugation and lysed via high pressure using a homogenizer. Cell lysates were centrifuged to remove cell debris and subsequently the cell lysates were stored at reduced temperature (e.g. −80° C.) until purification. Soluble Sortase was purified using Ni-NTA chromatography followed by size exclusion chromatography. For depletion of endotoxins an anion exchange chromatography was performed in flow through mode. The protein concentration of sortase preparations was determined by measuring the optical density (OD) at 280 nm, using the molar extinction coefficient calculated on the basis of the amino acid sequence. Purity and integrity of sortase was determined by SDS-PAGE in the presence and absence of a reducing agent (5 mM 1,4-dithiotreitol) and staining with Coomassie brilliant blue.

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue.

Example 3

Generation of an Expression Plasmid for C-Terminally Modified Fc-Region Polypeptides The expression plasmid for the transient expression of C-terminally modified Fc-region polypeptides (LPXTG or LPXTA) in HEK293 cells comprised besides the Fc-region expression cassette an origin of replication from the vector pUC18, which allows replication of this plasmid in *E. coli*, and a beta-lactamase gene which confers ampicillin resistance in *E. coli*.

The transcription unit of the Fc region polypeptide comprised the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- an N-terminally truncated *S. aureus* sortase A encoding nucleic acid, and
- the bovine growth hormone polyadenylation sequence (BGH pA).

Example 4

Transient Expression of Fc-Region Polypeptides

The recombinant production was performed by transient transfection of HEK293 cells (human embryonic kidney cell line 293-derived) cultivated in F17 Medium (Invitrogen Corp.). For transfection "293-Fectin" Transfection Reagent (Invitrogen) was used. Transfection was performed as specified in the manufacturer's instructions. Cell culture supernatants were harvested three to seven (3-7) days after transfection. Supernatants were stored at reduced temperature (e.g. −80° C.).

General information regarding the recombinant expression of human immunoglobulins in e.g. HEK293 cells is given in: Meissner, P. et al., Biotechnol. Bioeng. 75 (2001) 197-203.

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue.

Example 5

Sortase Mediated Simultaneous Conjugation

For the sortase-mediated transpeptidation reaction, N-terminally truncated *Staphylococcus aureus* Sortase A ($\Delta_{1-59}SrtA_{staph}$) and N-terminally truncated *Streptococcus pyogenes* Sortase A ($\Delta_{1-59}SrtA_{step}$) was used.

The reaction was performed in a buffer containing 50 mM Tris-HCl, 150 mM NaCl, pH 7.5 (Sortase-buffer).

The employed polypeptides were:
(1) an Fc-region polypeptide with the amino acid sequence LPETG (SEQ ID NO: 30) at its C-terminus,
(2) an Fc-region polypeptide with the amino acid sequence LPETA (SEQ ID NO: 32) at its C-terminus,
3) a polypeptide with two N-termini with the amino acid sequence H2N-GGG-GSGSK(GSGS-AAA-NH2)-COOH (SEQ ID NO: 33).

The following polypeptide/enzyme combinations, concentrations and sequences were tested:

| experiment | compound | concentration | calcium |
|---|---|---|---|
| 1 | LPETG-Fc-region polypeptide | 25 µM | 5 mM |
|   | LPETA-Fc-region polypeptide | 25 µM | |
|   | di-N-terminal polypeptide | 100 µM | |
|   | SrtA derived from S. aureus | 10 µM | |
|   | SrtA derived from S. pyogenes | 40 µM | |
| 2 | LPETG-Fc-region polypeptide | — | — |
|   | LPETA-Fc-region polypeptide | 25 µM | |
|   | di-N-terminal polypeptide | 100 µM | |

-continued

| experiment | compound | concentration | calcium |
|---|---|---|---|
| | SrtA derived from S. aureus | — | |
| | SrtA derived from S. pyogenes | 40 µM | |
| 3 | LPETG-Fc-region polypeptide | — | 5 mM |
| | LPETA-Fc-region polypeptide | 25 µM | |
| | di-N-terminal polypeptide | 100 µM | |
| | SrtA derived from S. aureus | — | |
| | SrtA derived from S. pyogenes | 40 µM | |
| 4 | LPETG-Fc-region polypeptide | 25 µM | 5 mM |
| | LPETA-Fc-region polypeptide (24 h) | 15 µM (*) | |
| | di-N-terminal polypeptide | 100 µM | |
| | SrtA derived from S. aureus | 10 µM | |
| | SrtA derived from S. pyogenes (24 h) | 24 µM (*) | |
| 5 | LPETG-Fc-region polypeptide (48 h) | 15 µM (*) | 5 mM |
| | LPETA-Fc-region polypeptide | 25 µM | (48h) |
| | di-N-terminal polypeptide | 100 µM | |
| | SrtA derived from S. aureus (48 h) | 6 µM (*) | |
| | SrtA derived from S. pyogenes | 40 µM | |
| 6 | LPETG-Fc-region polypeptide (48 h) | 15 µM (*) | 5 mM |
| | LPETA-Fc-region polypeptide | 25 µM | |
| | di-N-terminal polypeptide | 100 µM | |
| | SrtA derived from S. aureus (48 h) | 6 µM (*) | |
| | SrtA derived from S. pyogenes | 40 µM | |
| 7 | LPETG-Fc-region polypeptide (48 h) | 84 µM | 5 mM |
| | LPETA-Fc-region polypeptide | 84 µM | |
| | di-N-terminal polypeptide | 84 µM | |
| | SrtA derived from S. aureus (48 h) | 10 µM | |
| | SrtA derived from S. pyogenes | 40 µM | |
| 8 | LPETG-Fc-region polypeptide (48 h) | 50 µM | 5 mM |
| | LPETA-Fc-region polypeptide | 50 µM | |
| | di-N-terminal polypeptide | 50 µM | |
| | SrtA derived from S. aureus (48 h) | 10 µM | |
| | SrtA derived from S. pyogenes | 40 µM | |

Figure 1B:
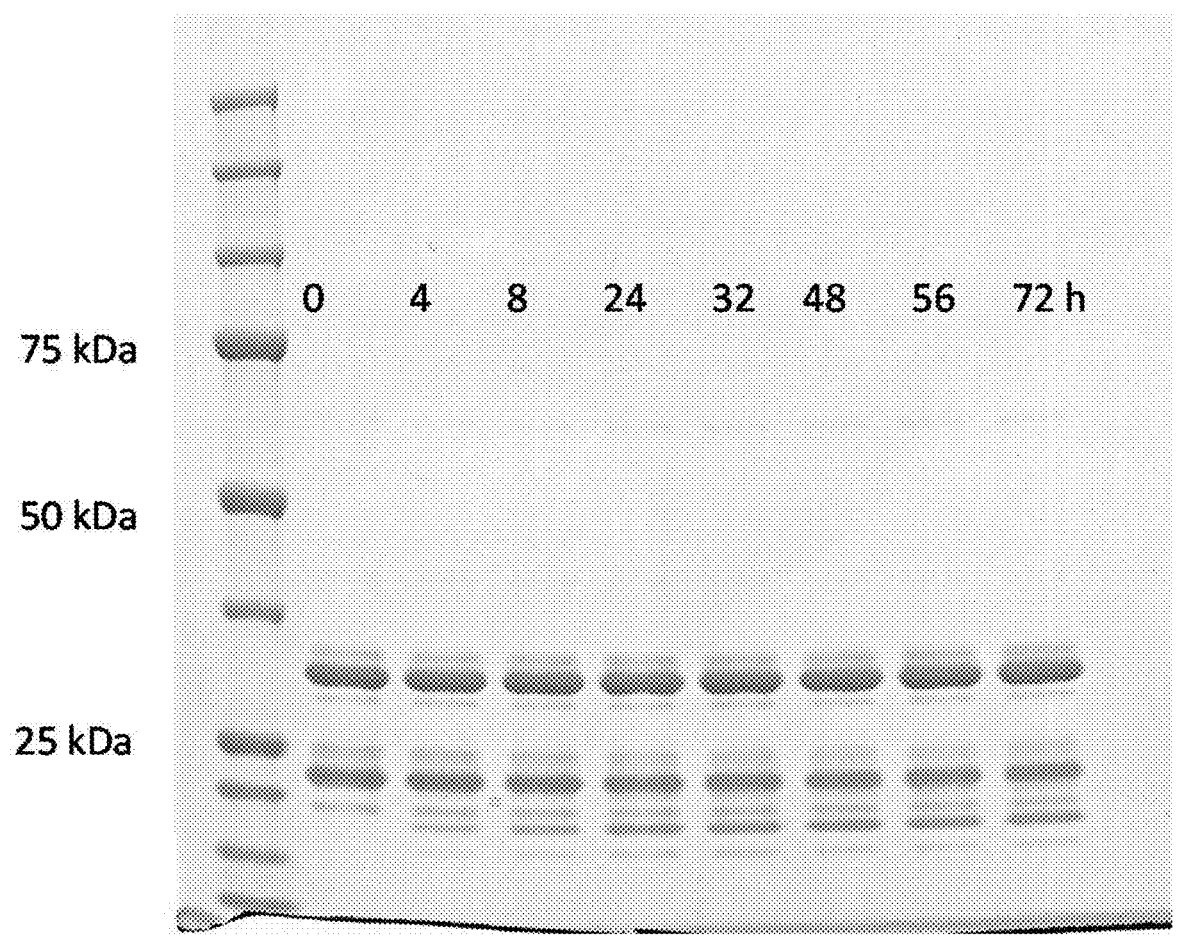
Figure 1C:
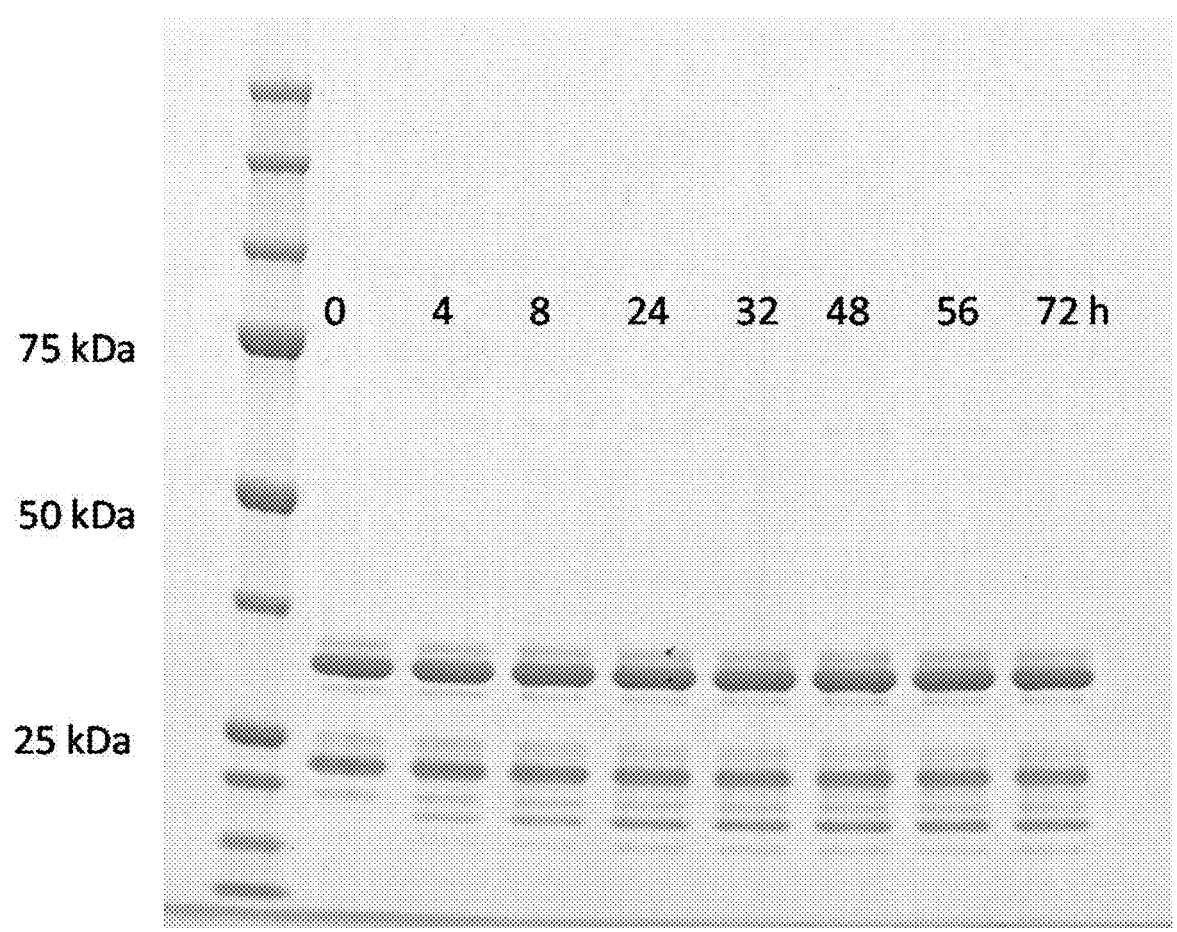
Figure 1D:
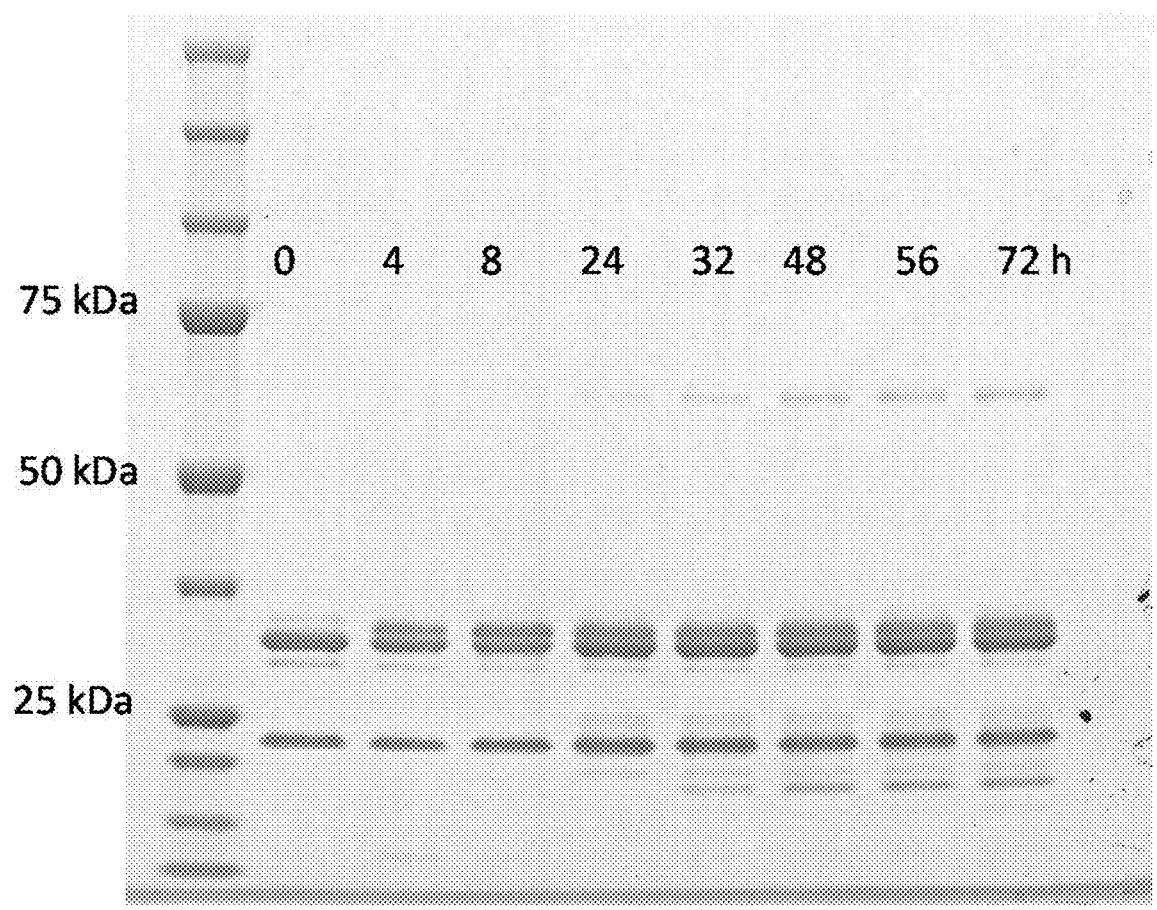
Figure 1E:
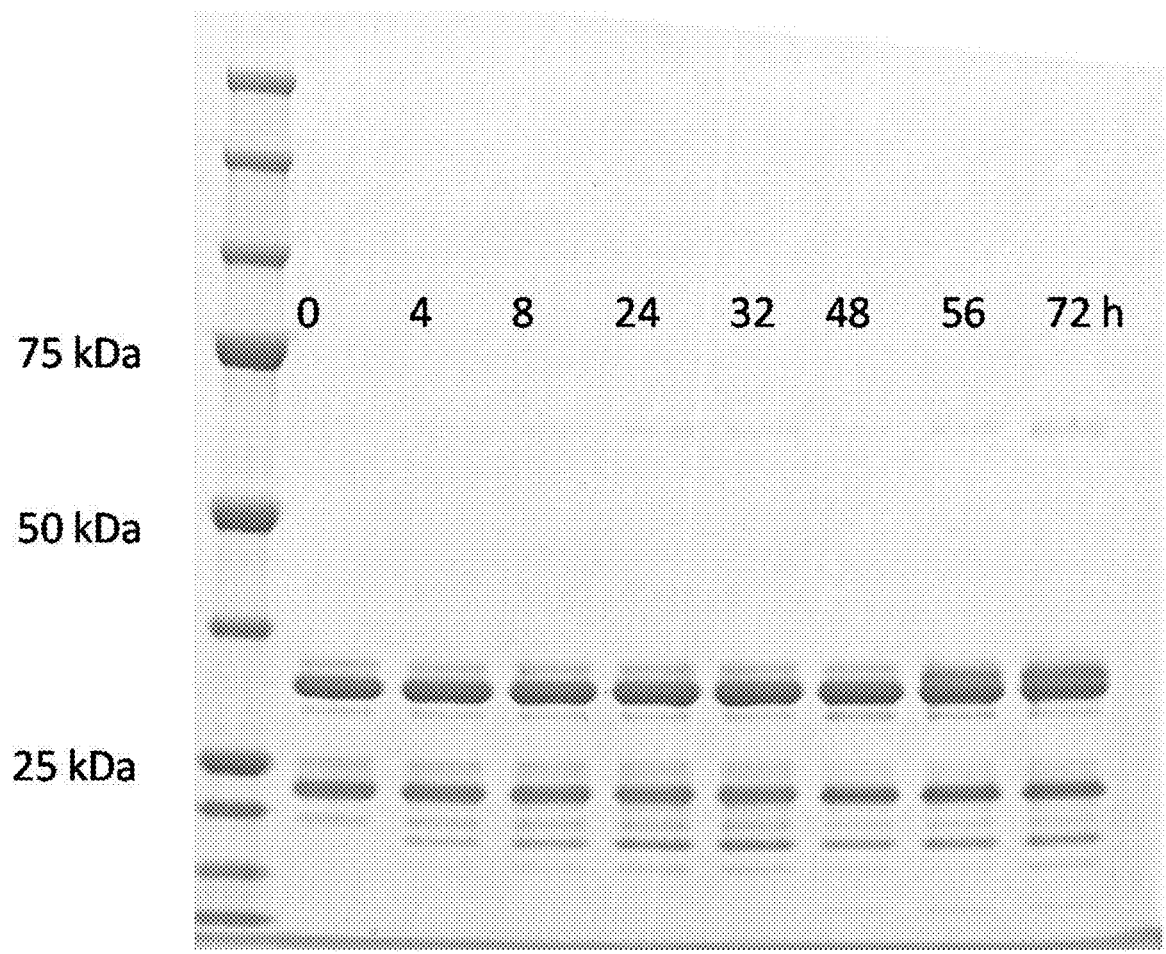
Figure 1F:
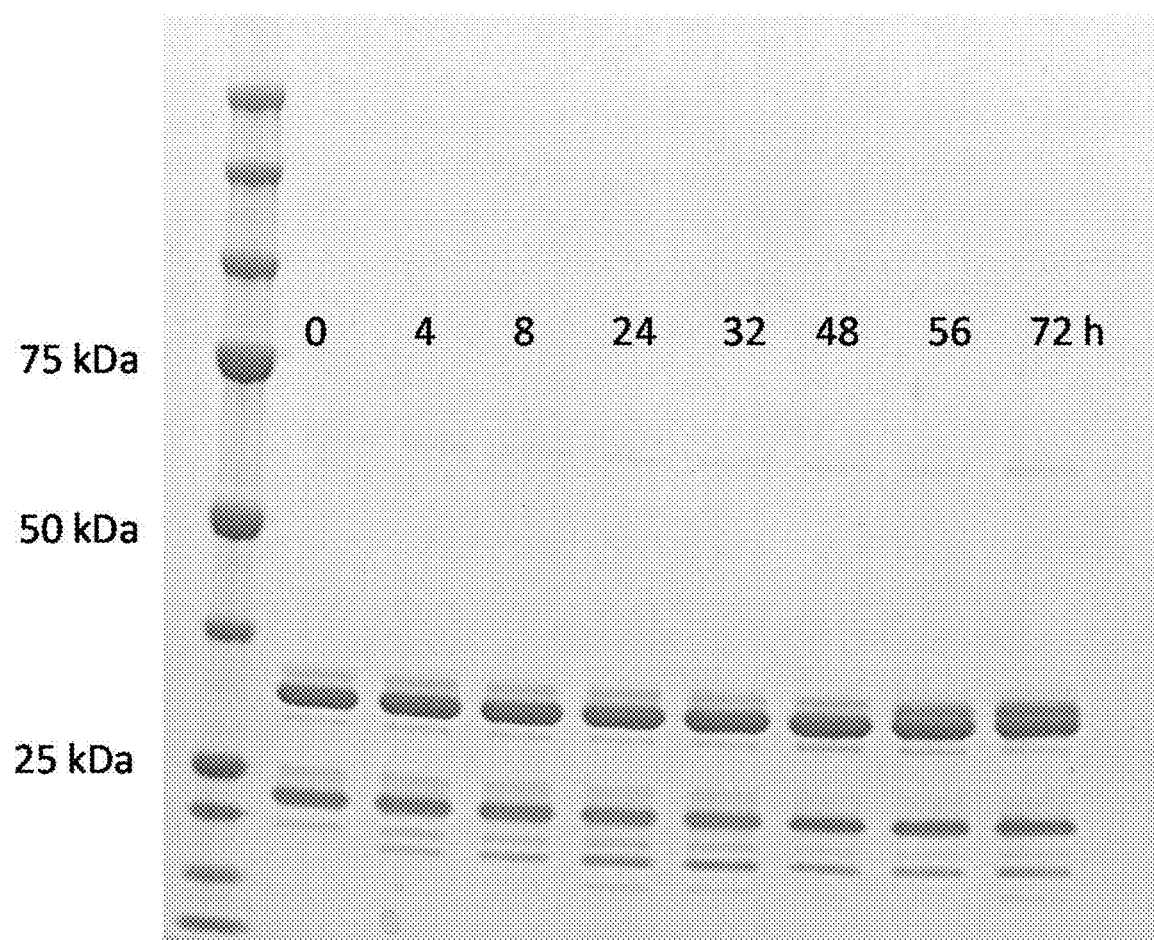
Figure 1G:
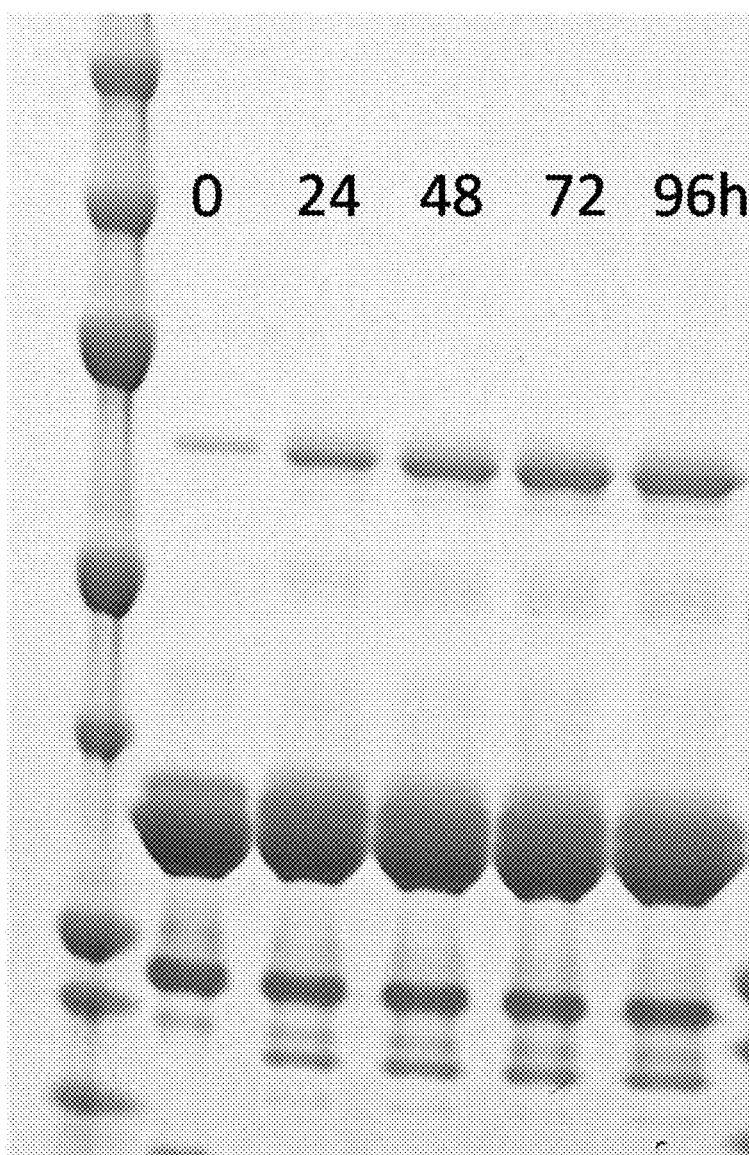
Figure 1H:
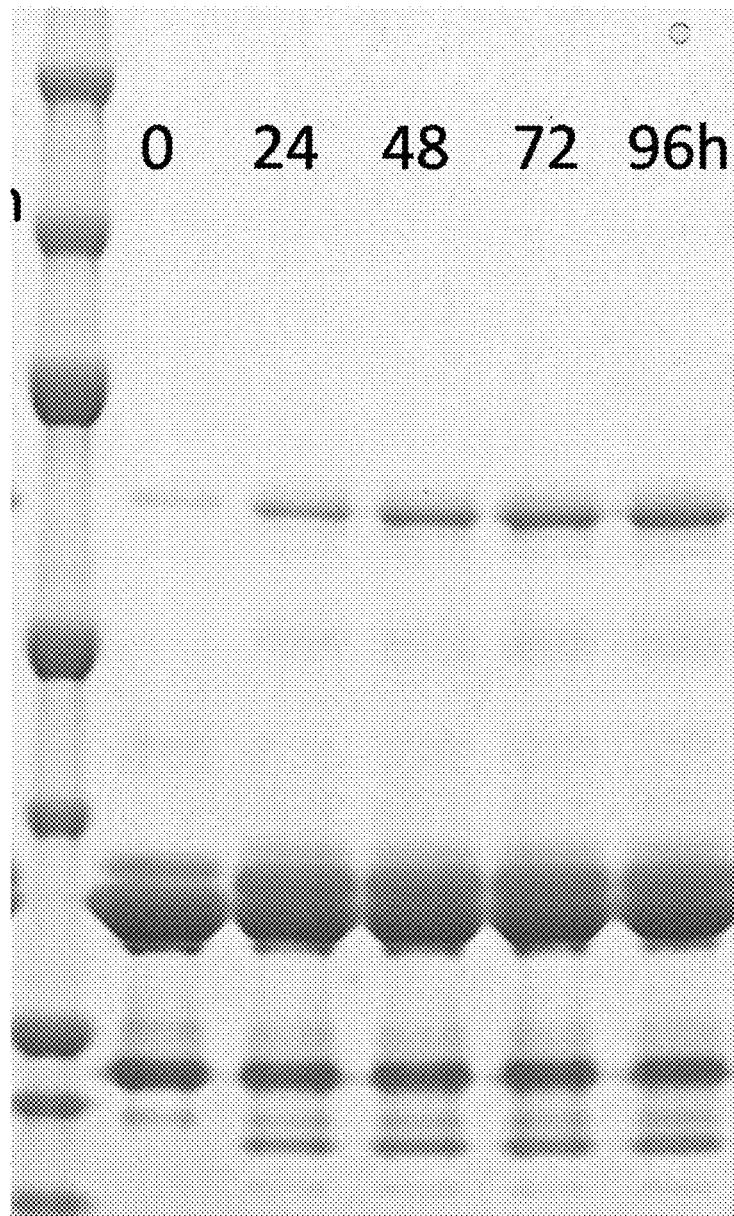
Figure 2:
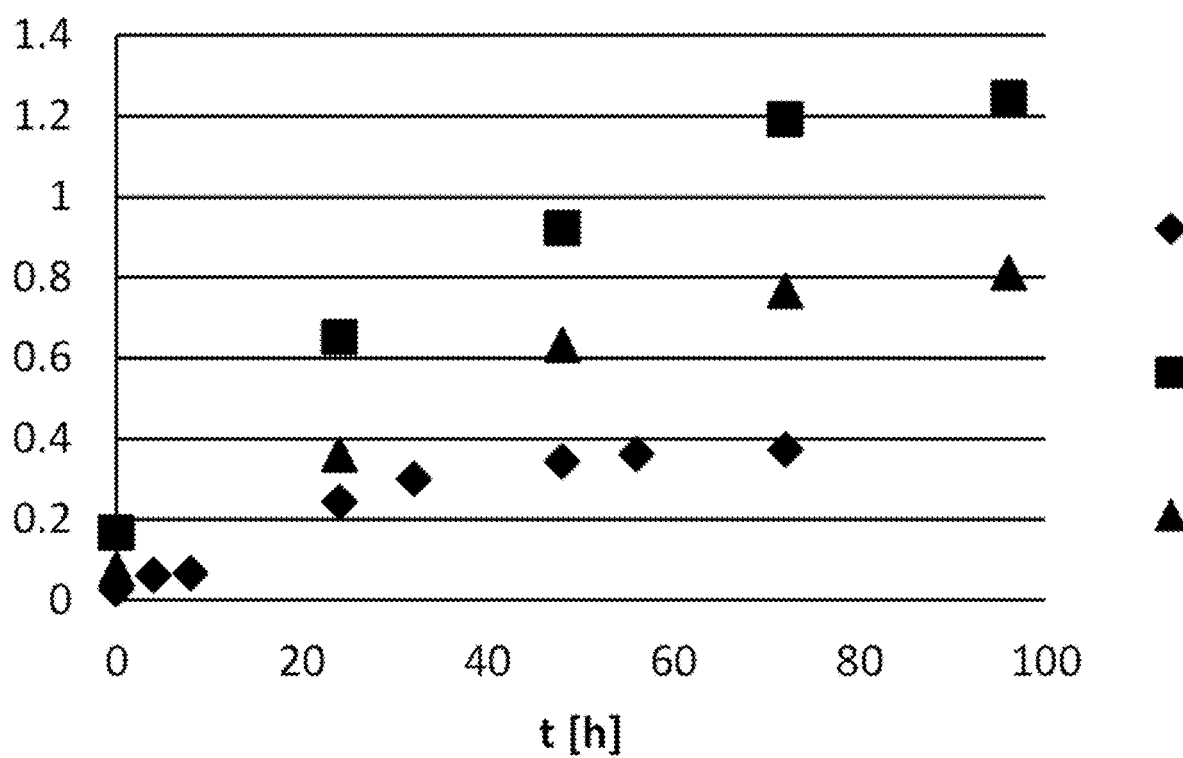
FIG. 2 Time course of the formation of the conjugate comprising the three polypeptides of experiments 1, 7 and 8 of Example 1; diamond: experiment 1, square: experiment 7, triangle: experiment 8; y-axis: amount of two times conjugated product normalized based on sortase amount.

—: this compound was not added to the reaction mixture
(24 h): this compound was added 24 hours after the reaction was started
(*): the concentrations are reduced (compared to the reactions where all components are mixed at the beginning) as the concentration of the di-N-terminal polypeptide is reduced due to the volume change of the second SrtA/the second Fc-region polypeptide and due to the reduction of the total volume by the sampling Samples from each experiment were taken after 0, 4, 8, 24, 32, 48, 56 and 72 hours and analyzed via SDS-page gel electrophoresis (2 µL sample, 1 µL DTT, 2.5 µL LDS, 4.5 µL $H_2O$, 70° C. 10 min.). The expected molecular weights are about 22 kDa for the SrtA, about 30 kDa for the Fc-region polypeptides and the single conjugated product (+1106 Da) and about 60 kDa for the conjugated comprising all three moieties. The results are shown in FIG. 1.

It can be seen that the simultaneous conjugation of two Fc-region polypeptides to a di-N-terminal polypeptide can be effected. The best results can be obtained in case all compounds (polypeptides and enzyme) are mixed at the beginning of the reaction. It can also be seen that the effect of the presence or absence of calcium in the reaction buffer is neglectable. It can further be seen that the use of equimolar amounts of all three polypeptides results in higher yield of the two-times conjugated product and at the same time the amount of single-conjugate product is reduced. Further it can be seen that if the polypeptides are employed at equimolar concentrations the higher the concentration the higher the yield. In experiment 8 the yield increases linearly until 72 hours reaction time and appears to reach a plateau at around 100 hours.

Example 6

Purification of the Double Conjugate

The double conjugate was purified from the reaction mix via size exclusion chromatography using a HiLoad 16/600 Superdex 200 prep grade column (GE Healthcare, Cat. No. 28-9893-35) and a 0.05 M $NaPO_4$ buffer comprising 0.15 M NaCl, pH 7.2. The sample volume was 0.3 mL and the loop-volume was 2.0 mL. Collection of 0.5 µL fractions was started after 20% of the column volume.

The invention claimed is:

1. A method for producing an enzymatic conjugation product of three polypeptides comprising incubating simultaneously
    a) i) a first polypeptide comprising the amino acid sequence LPXTG (SEQ ID NO: 20), wherein X can be any amino acid residue,
    ii) a second polypeptide comprising the amino acid sequence LPXTA (SEQ ID NO: 31), wherein X can be any amino acid residue,
    iii) a third polypeptide that is an antibody Fc-region wherein the polypeptide has an oligo-glycine at its first N-terminus, wherein said oligo-glycine comprises SEQ ID NO: 22, SEQ ID NO: 23, SEQ ID NO: 24, or SEQ ID NO: 25, and an oligo-alanine at its second N-terminus, wherein said oligo-alanine comprises SEQ ID NO: 26, SEQ ID NO: 27, SEQ ID NO: 28, or SEQ ID NO: 29,
    iv) *Staphylococcus aureus* sortase A, and
    v) *Streptococcus pyogenes* sortase A;
    b) i) a first polypeptide comprising the amino acid sequence LPXTG (SEQ ID NO: 20), wherein X can be any amino acid residue,
    ii) a second polypeptide that has an oligo-glycine at its N-terminus, wherein said oligo-glycine comprises SEQ ID NO: 22, SEQ ID NO: 23, SEQ ID NO: 24, or SEQ ID NO: 25, and that comprises the amino acid sequence LPXTA (SEQ ID NO: 31), wherein X can be any amino acid residue,
    iii) a third polypeptide that has an oligo-alanine at its N-terminus, wherein said oligo-alanine comprises SEQ ID NO: 26, SEQ ID NO: 27, SEQ ID NO: 28, or SEQ ID NO: 29,
    iv) *Staphylococcus aureus* sortase A, and
    v) *Streptococcus pyogenes* sortase A;
    or
    c) i) a first polypeptide comprising the amino acid sequence LPXTA (SEQ ID NO: 31), wherein X can be any amino acid residue,
    ii) a second polypeptide that has an oligo-alanine at its N-terminus, wherein said oligo-alanine comprises SEQ ID NO: 26, SEQ ID NO: 27, SEQ ID NO: 28, or SEQ ID NO: 29, and that comprises the amino acid sequence LPXTG (SEQ ID NO: 20), wherein X can be any amino acid residue,
    iii) a third polypeptide that has an oligo-glycine at its N-terminus, wherein said oligo-glycine comprises SEQ ID NO: 22, SEQ ID NO: 23, SEQ ID NO: 24, or SEQ ID NO: 25,
    iv) *Staphylococcus aureus* sortase A, and
    v) *Streptococcus pyogenes* sortase A, and wherein said method further comprises recovering the enzymatic conjugation product of the three polypeptides obtained from the incubation steps of a), b), or c).

2. The method according to claim 1, wherein the first, second and third polypeptides in a), b), or c) are present at about equimolar concentration.

3. The method according to claim 1, wherein the oligo-alanine in a), b), or c) is a di-alanine (SEQ ID NO: 26) or a tri-alanine (SEQ ID NO: 27).

4. The method according to claim 1, wherein the oligo-glycine in a), b), or c) is a di-glycine (SEQ ID NO: 22) or a tri-glycine (SEQ ID NO: 23).

5. The method according to claim 1, wherein the *Staphylococcus aureus* sortase A in a), b), or c) has the amino acid sequence of SEQ ID NO: 21.

6. The method according to claim 1, wherein the *Streptococcus pyogenes* sortase A in a), b), or c) has the amino acid sequence of SEQ ID NO: 34.

7. The method according to claim 1, wherein the first polypeptide, the second polypeptide and the third polypeptides in a), b), and c) are independently of each other selected from an antibody variable domain, an antibody heavy chain Fab-fragment, an antibody Fc-region, and a tag.

8. The method according to claim 2, wherein the first polypeptide, the second polypeptide and the third polypeptides in a), b), and c) are independently of each other selected from an antibody variable domain, an antibody heavy chain Fab-fragment, an antibody Fc-region, and a tag.

9. The method according to claim 3, wherein the first polypeptide, the second polypeptide and the third polypeptides in a), b), and c) are independently of each other selected from an antibody variable domain, an antibody heavy chain Fab-fragment, an antibody Fc-region, and a tag.

10. The method according to claim 4, wherein the first polypeptide, the second polypeptide and the third polypeptides in a), b), and c) are independently of each other selected from an antibody variable domain, an antibody heavy chain Fab-fragment, an antibody Fc-region, and a tag.

11. The method according to claim 5, wherein the first polypeptide, the second polypeptide and the third polypeptides in a), b), and c) are independently of each other selected from an antibody variable domain, an antibody heavy chain Fab-fragment, an antibody Fc-region, and a tag.

12. The method according to claim 6, wherein the first polypeptide, the second polypeptide and the third polypeptides in a), b), and c) are independently of each other selected from an antibody variable domain, an antibody heavy chain Fab-fragment, an antibody Fc-region, and a tag.

* * * * *

SEQUENCE LISTING

```
<160> NUMBER OF SEQ ID NOS: 36

<210> SEQ ID NO 1
<211> LENGTH: 5
<212> TYPE: PRT
<213> ORGANISM: Artificial Sequence
<220> FEATURE:
<223> OTHER INFORMATION: Arg-tag

<400> SEQUENCE: 1

Arg Arg Arg Arg Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Arg-tag 2

<400> SEQUENCE: 2

Arg Arg Arg Arg Arg Arg
1               5

<210> SEQ ID NO 3
<211> LENGTH: 6
<212> TYPE: PRT
<213> ORGANISM: Artificial Sequence
<220> FEATURE:
```

```
<223> OTHER INFORMATION: His-tag

<400> SEQUENCE: 3

His His His His His His
1               5

<210> SEQ ID NO 4
<211> LENGTH: 19
<212> TYPE: PRT
<213> ORGANISM: Artificial Sequence
<220> FEATURE:
<223> OTHER INFORMATION: amino acid tag

<400> SEQUENCE: 4

Lys Asp His Leu Ile His Asn Val His Lys Glu Phe His Ala His Ala
1               5                   10                  15

His Asn Lys

<210> SEQ ID NO 5
<211> LENGTH: 8
<212> TYPE: PRT
<213> ORGANISM: Artificial Sequence
<220> FEATURE:
<223> OTHER INFORMATION: amino acid tag

<400> SEQUENCE: 5

Asp Tyr Lys Asp Asp Asp Asp Lys
1               5

<210> SEQ ID NO 6
<211> LENGTH: 22
<212> TYPE: PRT
<213> ORGANISM: Artificial Sequence
<220> FEATURE:
<223> OTHER INFORMATION: amino acid tag

<400> SEQUENCE: 6

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 7
<211> LENGTH: 9
<212> TYPE: PRT
<213> ORGANISM: Artificial Sequence
<220> FEATURE:
<223> OTHER INFORMATION: amino acid tag#

<400> SEQUENCE: 7

Ala Trp Arg His Pro Gln Phe Gly Gly
1               5

<210> SEQ ID NO 8
<211> LENGTH: 8
<212> TYPE: PRT
<213> ORGANISM: Artificial Sequence
<220> FEATURE:
<223> OTHER INFORMATION: amino acid tag

<400> SEQUENCE: 8

Trp Ser His Pro Gln Phe Glu Lys
1               5

<210> SEQ ID NO 9
```

```
<211> LENGTH: 10
<212> TYPE: PRT
<213> ORGANISM: Artificial Sequence
<220> FEATURE:
<223> OTHER INFORMATION: amino acid tag

<400> SEQUENCE: 9

Met Asp Val Glu Ala Trp Leu Gly Ala Arg
1               5                   10

<210> SEQ ID NO 10
<211> LENGTH: 16
<212> TYPE: PRT
<213> ORGANISM: Artificial Sequence
<220> FEATURE:
<223> OTHER INFORMATION: amino acid tag

<400> SEQUENCE: 10

Met Asp Val Glu Ala Trp Leu Gly Ala Arg Val Pro Leu Val Glu Thr
1               5                   10                  15

<210> SEQ ID NO 11
<211> LENGTH: 38
<212> TYPE: PRT
<213> ORGANISM: Artificial Sequence
<220> FEATURE:
<223> OTHER INFORMATION: amino acid tag

<400> SEQUENCE: 11

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 12
<211> LENGTH: 10
<212> TYPE: PRT
<213> ORGANISM: Artificial Sequence
<220> FEATURE:
<223> OTHER INFORMATION: amino acid tag

<400> SEQUENCE: 12

Glu Gln Lys Leu Ile Ser Glu Glu Asp Leu
1               5                   10

<210> SEQ ID NO 13
<211> LENGTH: 15
<212> TYPE: PRT
<213> ORGANISM: Artificial Sequence
<220> FEATURE:
<223> OTHER INFORMATION: amino acid tag

<400> SEQUENCE: 13

Lys Glu Thr Ala Ala Ala Lys Phe Glu Arg Gln His Met Asp Ser
1               5                   10                  15

<210> SEQ ID NO 14
<211> LENGTH: 26
<212> TYPE: PRT
<213> ORGANISM: Artificial Sequence
<220> FEATURE:
<223> OTHER INFORMATION: amino acid tag

<400> SEQUENCE: 14
```

```
Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

<210> SEQ ID NO 15
<211> LENGTH: 47
<212> TYPE: PRT
<213> ORGANISM: Artificial Sequence
<220> FEATURE:
<223> OTHER INFORMATION: amino acid tag

<400> SEQUENCE: 15

```
Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
            20                  25                  30

Gly Thr Thr Cys Gln Val Leu Asn Pro Tyr Tyr Ser Gln Cys Leu
        35                  40                  45
```

<210> SEQ ID NO 16
<211> LENGTH: 32
<212> TYPE: PRT
<213> ORGANISM: Butyrivibrio fibrisolvens

<400> SEQUENCE: 16

```
Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
            20                  25                  30
```

<210> SEQ ID NO 17
<211> LENGTH: 51
<212> TYPE: PRT
<213> ORGANISM: Artificial Sequence
<220> FEATURE:
<223> OTHER INFORMATION: chitin-binding-domain

<400> SEQUENCE: 17

```
Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50
```

<210> SEQ ID NO 18
<211> LENGTH: 209
<212> TYPE: PRT
<213> ORGANISM: Chondrus crispus

<400> SEQUENCE: 18

```
Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
            20                  25                  30

Arg Val Val Phe Asp His Trp Lys Glu Ala Lys Pro Lys Thr Pro Tyr
        35                  40                  45

Ala Ala Leu Pro Met Leu Thr Val Asp Gly Met Gln Val Ala Gln Ser
```

```
                50                  55                  60
Asp Ala Ile Leu Arg Tyr Cys Gly Lys Leu Ala Gly Leu Tyr Pro Ser
 65                  70                  75                  80

Asp Pro Leu Glu Ala Ala Lys Val Asp Glu Val Gly Val Ile Asp
                 85                  90                  95

Asp Val Thr His Ala Met Tyr Arg Tyr Arg Gly Asp Asp Lys Asp Lys
                100                 105                 110

Leu Arg Glu Glu Arg Asp Lys Phe Ser Lys Val Asp Val Pro Arg Tyr
                115                 120                 125

Val Gly Ala Leu Glu Lys Arg Leu Glu Ala Phe Gly Asp Gly Pro Trp
                130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Asp Lys Asp Leu
                165                 170                 175

Leu Glu Gly Tyr Val Arg Ile Val Lys Ser Tyr Ser Ala Val Met Glu
                180                 185                 190

His Pro Lys Val Thr Glu Trp Tyr Glu Lys Lys Pro Val Lys Met Phe
                195                 200                 205

Ser

<210> SEQ ID NO 19
<211> LENGTH: 396
<212> TYPE: PRT
<213> ORGANISM: Escherichia coli

<400> SEQUENCE: 19

Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly Lys
                 20                  25                  30

Leu Val Ile Trp Ile Asn Gly Asp Lys Gly Tyr Asn Gly Leu Ala Glu
                 35                  40                  45

Val Gly Lys Lys Phe Glu Lys Asp Thr Gly Ile Lys Val Thr Val Glu
 50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
                115                 120                 125

Leu Ile Ala Tyr Pro Ile Ala Val Glu Ala Leu Ser Leu Ile Tyr Asn
                130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
                195                 200                 205

Val Asp Asn Ala Gly Ala Lys Ala Gly Leu Thr Phe Leu Val Asp Leu
```

```
                        210                 215                 220
Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys
385                 390                 395

<210> SEQ ID NO 20
<211> LENGTH: 5
<212> TYPE: PRT
<213> ORGANISM: Artificial Sequence
<220> FEATURE:
<223> OTHER INFORMATION: sortase amino acid motif of Staphylococcus
      aureus
<220> FEATURE:
<221> NAME/KEY: MISC_FEATURE
<222> LOCATION: (3)..(3)
<223> OTHER INFORMATION: Xaa = can be any of the 20 proteinogenic amino
      acids

<400> SEQUENCE: 20

Leu Pro Xaa Thr Gly
1               5

<210> SEQ ID NO 21
<211> LENGTH: 147
<212> TYPE: PRT
<213> ORGANISM: Artificial Sequence
<220> FEATURE:
<223> OTHER INFORMATION: mature soluble sortase

<400> SEQUENCE: 21

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
                20                  25                  30

Ala Thr Pro Glu Gln Leu Asn Arg Gly Val Ser Phe Ala Glu Glu Asn
            35                  40                  45

Glu Ser Leu Asp Asp Gln Asn Ile Ser Ile Ala Gly His Thr Phe Ile
        50                  55                  60

Asp Arg Pro Asn Tyr Gln Phe Thr Asn Leu Lys Ala Ala Lys Lys Gly
65                  70                  75                  80
```

```
Ser Met Val Tyr Phe Lys Val Gly Asn Glu Thr Arg Lys Tyr Lys Met
                85                  90                  95

Thr Ser Ile Arg Asp Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Lys Arg Lys Ile Phe Val Ala Thr
    130                 135                 140

Glu Val Lys
145

<210> SEQ ID NO 22
<211> LENGTH: 2
<212> TYPE: PRT
<213> ORGANISM: Artificial Sequence
<220> FEATURE:
<223> OTHER INFORMATION: oligoglycine motif

<400> SEQUENCE: 22

Gly Gly
1

<210> SEQ ID NO 23
<211> LENGTH: 3
<212> TYPE: PRT
<213> ORGANISM: Artificial Sequence
<220> FEATURE:
<223> OTHER INFORMATION: oligoglycine motif

<400> SEQUENCE: 23

Gly Gly Gly
1

<210> SEQ ID NO 24
<211> LENGTH: 4
<212> TYPE: PRT
<213> ORGANISM: Artificial Sequence
<220> FEATURE:
<223> OTHER INFORMATION: oligoglycine motif

<400> SEQUENCE: 24

Gly Gly Gly Gly
1

<210> SEQ ID NO 25
<211> LENGTH: 5
<212> TYPE: PRT
<213> ORGANISM: Artificial Sequence
<220> FEATURE:
<223> OTHER INFORMATION: oligoglycine motif

<400> SEQUENCE: 25

Gly Gly Gly Gly Gly
1               5

<210> SEQ ID NO 26
<211> LENGTH: 2
<212> TYPE: PRT
<213> ORGANISM: Artificial Sequence
<220> FEATURE:
<223> OTHER INFORMATION: oligoalanine motif

<400> SEQUENCE: 26

Ala Ala
1
```

```
<210> SEQ ID NO 27
<211> LENGTH: 3
<212> TYPE: PRT
<213> ORGANISM: Artificial Sequence
<220> FEATURE:
<223> OTHER INFORMATION: oligoalanine motif

<400> SEQUENCE: 27

Ala Ala Ala
1

<210> SEQ ID NO 28
<211> LENGTH: 4
<212> TYPE: PRT
<213> ORGANISM: Artificial Sequence
<220> FEATURE:
<223> OTHER INFORMATION: oligoalanine motif

<400> SEQUENCE: 28

Ala Ala Ala Ala
1

<210> SEQ ID NO 29
<211> LENGTH: 5
<212> TYPE: PRT
<213> ORGANISM: Artificial Sequence
<220> FEATURE:
<223> OTHER INFORMATION: oligoalanine motif

<400> SEQUENCE: 29

Ala Ala Ala Ala Ala
1               5

<210> SEQ ID NO 30
<211> LENGTH: 5
<212> TYPE: PRT
<213> ORGANISM: Artificial Sequence
<220> FEATURE:
<223> OTHER INFORMATION: sortase motif

<400> SEQUENCE: 30

Leu Pro Glu Thr Gly
1               5

<210> SEQ ID NO 31
<211> LENGTH: 5
<212> TYPE: PRT
<213> ORGANISM: Artificial Sequence
<220> FEATURE:
<223> OTHER INFORMATION: sortase amino acid motif of sortase from
      Streptococcus pyogenes
<220> FEATURE:
<221> NAME/KEY: MISC_FEATURE
<222> LOCATION: (3)..(3)
<223> OTHER INFORMATION: Xaa can be any one of the 20 protenaceous amino
      acid residues

<400> SEQUENCE: 31

Leu Pro Xaa Thr Ala
1               5

<210> SEQ ID NO 32
<211> LENGTH: 5
<212> TYPE: PRT
<213> ORGANISM: Artificial Sequence
<220> FEATURE:
<223> OTHER INFORMATION: sortase motif LPETA
```

<400> SEQUENCE: 32

Leu Pro Glu Thr Ala
1               5

<210> SEQ ID NO 33
<211> LENGTH: 8
<212> TYPE: PRT
<213> ORGANISM: Artificial Sequence
<220> FEATURE:
<223> OTHER INFORMATION: bi-N-terminal polypeptide
<220> FEATURE:
<221> NAME/KEY: PEPTIDE
<222> LOCATION: (8)..(8)
<223> OTHER INFORMATION: conjugated via the epsilon amino group -
      GSGSAAA

<400> SEQUENCE: 33

Gly Gly Gly Gly Ser Gly Ser Lys
1               5

<210> SEQ ID NO 34
<211> LENGTH: 168
<212> TYPE: PRT
<213> ORGANISM: Artificial Sequence
<220> FEATURE:
<223> OTHER INFORMATION: soluble Streptococcus pyogenes Sortase A

<400> SEQUENCE: 34

Val Leu Gln Ala Gln Met Ala Ala Gln Gln Leu Pro Val Ile Gly Gly
1               5                   10                  15

Ile Ala Ile Pro Glu Leu Gly Ile Asn Leu Pro Ile Phe Lys Gly Leu
                20                  25                  30

Gly Asn Thr Glu Leu Ile Tyr Gly Ala Gly Thr Met Lys Glu Glu Gln
            35                  40                  45

Val Met Gly Gly Glu Asn Asn Tyr Ser Leu Ala Ser His His Ile Phe
    50                  55                  60

Gly Ile Thr Gly Ser Ser Gln Met Leu Phe Ser Pro Leu Glu Arg Ala
65                  70                  75                  80

Gln Asn Gly Met Ser Ile Tyr Leu Thr Asp Lys Glu Lys Ile Tyr Glu
                85                  90                  95

Tyr Ile Ile Lys Asp Val Phe Thr Val Ala Pro Glu Arg Val Asp Val
            100                 105                 110

Ile Asp Asp Thr Ala Gly Leu Lys Glu Val Thr Leu Val Thr Cys Thr
        115                 120                 125

Asp Ile Glu Ala Thr Glu Arg Ile Ile Val Lys Gly Glu Leu Lys Thr
    130                 135                 140

Glu Tyr Asp Phe Asp Lys Ala Pro Ala Asp Val Leu Lys Ala Phe Asn
145                 150                 155                 160

His Ser Tyr Asn Gln Val Ser Thr
                165

<210> SEQ ID NO 35
<211> LENGTH: 4
<212> TYPE: PRT
<213> ORGANISM: Artificial Sequence
<220> FEATURE:
<223> OTHER INFORMATION: EPEA

<400> SEQUENCE: 35

Glu Pro Glu Ala
1

```
<210> SEQ ID NO 36
<211> LENGTH: 12
<212> TYPE: PRT
<213> ORGANISM: Artificial Sequence
<220> FEATURE:
<223> OTHER INFORMATION: purification tag

<400> SEQUENCE: 36

Met Arg Gly Ser His His His His His His Gly Ser
1               5                   10
```